(12) United States Patent
Zentner et al.

(10) Patent No.: US 8,653,139 B2
(45) Date of Patent: Feb. 18, 2014

(54) DRUG SUBSTANCE PREPARATIONS, PHARMACEUTICAL COMPOSITIONS AND DOSAGE FORMS

(75) Inventors: Gaylen M. Zentner, Salt Lake City, UT (US); James C. McRea, Salt Lake City, UT (US); Mark S. Williams, Salt Lake City, UT (US); Stephen J. Martin, Rothbury (GB); Norman T. Smith, Bedlington (GB); Catriona A. Oare, Baldock (GB)

(73) Assignee: Aesica Pharmaceuticals Limited, Cramlington, Northumberland (GB)

( * ) Notice: Subject to any disclaimer, the term of this patent is extended or adjusted under 35 U.S.C. 154(b) by 139 days.

(21) Appl. No.: 12/533,323

(22) Filed: Jul. 31, 2009

(65) Prior Publication Data
US 2010/0087538 A1 Apr. 8, 2010

Related U.S. Application Data

(63) Continuation of application No. PCT/US2008/052853, filed on Feb. 1, 2008.

(60) Provisional application No. 60/887,733, filed on Feb. 1, 2007.

(51) Int. Cl.
*A61K 31/19* (2006.01)

(52) U.S. Cl.
USPC ........................................................ 514/568

(58) Field of Classification Search
USPC ........................................................ 514/568
See application file for complete search history.

(56) References Cited

U.S. PATENT DOCUMENTS

| | | |
|---|---|---|
| 3,755,427 A | 8/1973 | Adams et al. |
| 3,959,364 A | 5/1976 | Armitage et al. |
| 4,209,638 A | 6/1980 | Nicholson et al. |
| 4,983,765 A | 1/1991 | Lukas et al. |
| 5,015,764 A | 5/1991 | Manimaran et al. |
| 5,235,100 A | 8/1993 | Choudhury et al. |
| 5,510,519 A | 4/1996 | Yoneyoshi et al. |
| 5,574,183 A | 11/1996 | Patil et al. |
| 5,599,969 A | 2/1997 | Hardy et al. |
| 2005/0042284 A1 * | 2/2005 | Hobden et al. ................ 424/464 |

OTHER PUBLICATIONS

International Search Report, PCT/US08/52853, mailed on May 22, 2008.
Medical News Today. Myriad Genetics Completes Enrollment in U.S. Phase 3 Climincal Trial of Flurizan for Alzheimer's Disease, Medical News Today, Aug. 23, 2006. http://www.medicalnewstoday.com/articles/50247.php , para 2.
Bauer et al. Purity as an issue in pharmaceutical research and development. Eur J Pharm Sci., 1998, pp. 331-335, especially p. 332, 2. Purity and specifications.

\* cited by examiner

*Primary Examiner* — San-Ming Hui
*Assistant Examiner* — Katherine Cruz
(74) *Attorney, Agent, or Firm* — Fangli Chen; Robert N. Sahr; Choate, Hall & Stewart LLP

(57) ABSTRACT

The invention relates to drug substance preparations, pharmaceutical compositions and dosage forms containing (R)-(−)-2-(2-fluoro-4-biphenylyl) propionic acid as the active pharmaceutical ingredient, and limited amounts of specific product-related and process-related impurities.

33 Claims, No Drawings

DRUG SUBSTANCE PREPARATIONS, PHARMACEUTICAL COMPOSITIONS AND DOSAGE FORMS

CROSS REFERENCE TO RELATED APPLICATIONS

This application is a continuation of International Application PCT/US2008/052853, filed Feb. 1, 2008, which claims priority to U.S. Provisional Application Ser. No. 60/887,733 filed Feb. 1, 2007, the contents of both of which are incorporated herein by reference in their entirety.

FIELD OF THE INVENTION

The invention relates to drug substance preparations, pharmaceutical compositions, and dosage forms.

BACKGROUND OF THE INVENTION

The development of all pharmaceutical products requires the production of high purity drug substance preparations, pharmaceutical compositions and dosage forms that contain effective amounts of the active pharmaceutical ingredient (API), and minimal impurities. However, pharmaceutical products containing an API that must be dosed in large amounts for long periods of time, present a special challenge to drug manufacturers since, in such cases, the potential exposure of the patient to any impurities present in the pharmaceutical product is amplified.

All drug substance preparations, regardless of the API, contain finite amounts of impurities. These impurities can generally be grouped into categories based upon their chemical identity.

Impurities that are structurally similar to the API are commonly referred to as "product-related impurities." In the case of APIs containing chiral centers where one enantiomer shows therapeutic effect, while the other enantiomer shows either no effect, minimal effect, or an undesirable effect, the latter enantiomer represents a type of product-related impurity, commonly referred to as an "enantiomeric impurity."

Impurities that are not structurally similar to the API, and are introduced by the process(es) used to make the API, are commonly referred to as "process-related impurities." Process-related impurities can comprise such things as unreacted starting materials, materials added to purify the API, by-products of side reactions, and the like, which do not structurally resemble the API. Process-related impurities may also comprise residual solvents and heavy metals. However, due to their known toxic properties, residual solvents and heavy metals are often considered apart from other types of process-related impurities.

Since drug substance preparations containing a given API are used to prepare pharmaceutical compositions, which, in turn are used to manufacture drug products for administration of the API, pharmaceutical compositions and drug products generally contain the product- and process-related impurities that co-occur with the given API in the starting drug substance preparations. In order to minimize risk to human health caused by impurities within drug products, governmental agencies establish specific limits for various types of impurities that arise in final drug products from the API-containing drug substance preparations. Drug substance preparations and excipients must typically have impurity levels that are equal to or less than these limits, in order for manufacturers to gain governmental approval to market and sell their drug products.

As with drug substance preparations of any synthetic organic API, drug substance preparations of (R)-(−)-2-(2-fluoro-4-biphenylyl) propionic acid (USAN and INN name: tarenflurbil) can contain product-related impurities (e.g., (S)-(+)-2-(2-fluoro-4-biphenylyl) propionic acid), process-related impurities, residual solvents, and heavy metals. Since there is a need for pharmaceutical dosage forms containing (R)-(−)-2-(2-fluoro-4-biphenylyl) propionic acid as the API, and since the API in these dosage forms may require administration in relatively large amounts for extended periods of time, there is a clear need for (R)-(−)-2-(2-fluoro-4-biphenylyl) propionic acid-containing pharmaceutical compositions and dosage forms made from (R)-(−)-2-(2-fluoro-4-biphenylyl) propionic acid drug substance preparations containing acceptable levels of impurities of all types.

BRIEF SUMMARY OF THE INVENTION

The invention relates to drug substance preparations, pharmaceutical compositions, and dosage forms that contain (R)-(−)-2-(2-fluoro-4-biphenylyl) propionic acid (USAN and INN name: Tarenflurbil) as the API, and contain limited amounts of specific impurities. The inventors have discovered drug substance preparations of (R)-(−)-2-(2-fluoro-4-biphenylyl) propionic acid having minimal impurities that allow for the production of pharmaceutical dosage forms or drug products containing about 100 mg, 200 mg, 400 mg, 800 mg, or more (R)-(−)-2-(2-fluoro-4-biphenylyl) propionic acid, that have desirable physical characteristics, that produce therapeutically desirable pharmacokinetic profiles in human subjects, and that contain limited quantities of product-related impurities, process-related impurities, residual solvents, and heavy metals.

The drug substance preparations, pharmaceutical compositions and dosage forms of the invention are especially useful for treating (and/or preventing) conditions such as Alzheimer's disease, that require the dosing of patients with large amounts (e.g., 800 mg, twice daily) of (R)-(−)-2-(2-fluoro-4-biphenylyl) propionic acid for extended periods of time (e.g., more than 10 years). Under such dosing regimens it is important to limit all types of impurities in the dosage forms or drug products given to patients. In particular, it is important to limit those product-related and process-related impurities that are introduced into the dosage form by way of the drug substance preparations that contain the API and are used to make the pharmaceutical compositions used to manufacture the dosage form or drug product.

Thus, in one aspect, the invention provides drug substance preparations containing (R)-(−)-2-(2-fluoro-4-biphenylyl) propionic acid, or a pharmaceutically acceptable salt thereof, as the API, and limited amounts of specific product-related impurities, process-related impurities, residual solvents and heavy metals. In one embodiment of this aspect, all of the impurities present in these drug substance preparations are limited to about 5%, 4%, 3%, 2%, 1%, or less of the total weight of the drug substance preparation (i.e., [sum of weight(s) of one or more impurities]/[total weight of drug substance preparation]×100% is less than 5%, 4%, 3%, 2%, 1%, or less). In another embodiment, the invention provides a drug substance preparation containing (R)-(−)-2-(2-fluoro-4-biphenylyl) propionic acid, or a pharmaceutically acceptable salt thereof, as the API, and about 2%, 1%, 0.5%, 0.25%, 0.1%, 0.05%, 0.025%, 0.01%, 0.005%, 0.0025%, or 0.001% of the total weight of the drug substance preparation as product-related impurities. In another embodiment, the invention provides a drug substance preparation having from 0.001%-0.01%, 0.005%-0.05%, 0.01%-0.1%, 0.05%-0.5%, or 0.1%-

1%, of any one specific impurity, by weight. In another embodiment, the invention provides a drug substance preparation having from 0.001%-0.01%, 0.005%-0.05%, 0.01%-0.1%, 0.05%-0.5%, 0.1%-1%, or 0.5%-5%, by weight, of the specific product-related impurities, process-related impurities, residual solvents and heavy metals identified herein.

In certain embodiments, the present invention comprises drug substance preparations containing (R)-(−)-2-(2-fluoro-4-biphenylyl) propionic acid as the API, and limited amounts of product-related impurities. In these embodiments, the product-related impurities that are present in limited amounts include, e.g., the enantiomeric impurity (S)-(+)-2-(2-fluoro-4-biphenylyl) propionic acid (which is also known as (S)-flurbiprofen), 2-(4-biphenylyl) propionic acid, and methyl (2-(2-fluoro-4-biphenylyl))propionate. In specific embodiments, the present invention comprises drug substance preparations wherein the amounts of 2-(4-biphenylyl) propionic acid, as well as the enantiomeric impurity (S)-(+)-2-(2-fluoro-4-biphenylyl) propionic acid, are limited below certain maximum levels. In other specific embodiments, the present invention comprises drug substance preparations wherein the amounts of both 2-(4-biphenylyl) propionic acid and methyl (2-(2-fluoro-4-biphenylyl))propionate, as well as the enantiomeric impurity (S)-(+)-2-(2-fluoro-4-biphenylyl) propionic acid, are limited below certain maximum levels. In certain embodiments, the present invention comprises drug substance preparations wherein, in addition to the amounts of one or two known product-related impurities, as well as the enantiomeric impurity (S)-(+)-2-(2-fluoro-4-biphenylyl) propionic acid, being limited below certain maximum levels, the amounts of specific process-related impurities are also limited below certain maximum levels. In these embodiments, the principle process-related impurity that is limited below certain maximum levels is (R)-(+)-α-methylbenzylamine (which is also known as (R)-(+)-1-phenylethylamine), which is used as a chiral crystallization agent to resolve and isolate (R)-(−)-2-(2-fluoro-4-biphenylyl) propionic acid from racemic flurbiprofen (i.e., (R,S)-2-(2-fluoro-4-biphenylyl) propionic acid). In other embodiments, additional process-related impurities that are limited below certain maximum levels include residual solvents, and/or heavy metals. In these embodiments, the residual solvents to be limited include, e.g., toluene, methanol, and n-heptane.

In a preferred embodiment of this aspect of the invention, the present invention comprises drug substance preparations containing (R)-(−)-2-(2-fluoro-4-biphenylyl) propionic acid as the API, limited amounts of three product-related impurities, including the enantiomeric impurity (S)-(+)-2-(2-fluoro-4-biphenylyl) propionic acid, 2-(4-biphenylyl) propionic acid, and methyl (2-(2-fluoro-4-biphenylyl))propionate, limited amounts of the process-related impurity (R)-(+)-α-methylbenzylamine, and limited amounts of residual solvents and heavy metals.

In a related aspect, the invention provides methods to resolve racemic flurbiprofen (i.e., (R,S)-2-(2-fluoro-4-biphenylyl) propionic acid) using chiral crystallization, in order to purify the API, (R)-(−)-2-(2-fluoro-4-biphenylyl) propionic acid, and prepare drug substance preparations containing the limited amounts of product-related impurities, process-related impurities, residual solvents and heavy metals, as described above.

In another aspect, the invention provides pharmaceutical compositions comprising the drug substance preparations described above in admixture with one or more pharmaceutically acceptable excipients. Consequently, in embodiments of these aspects of the invention, the pharmaceutical compositions of the invention comprise (R)-(−)-2-(2-fluoro-4-biphenylyl) propionic acid, or a pharmaceutically acceptable salt thereof, as the API, and further comprise limited quantities of product-related impurities, process-related impurities, residual solvents and heavy metals. In these embodiments, the present invention provides pharmaceutical compositions in which all of the impurities deriving from the drug substance preparations of the invention represent about 5%, 4%, 3%, 2%, 1%, 0.5%, 0.25% 0.1%, 0.05%, 0.025%, 0.01%, or less of the total weight of the pharmaceutical composition (i.e., [sum of weight(s) of impurities deriving from the drug substance preparation]/[total weight of pharmaceutical composition]×100%). In certain embodiments of this aspect, the invention provides pharmaceutical compositions containing (R)-(−)-2-(2-fluoro-4-biphenylyl) propionic acid, or a pharmaceutically acceptable salt thereof, as the API, and about 2%, 1%, 0.5%, 0.25%, 0.1%, 0.05%, 0.025%, 0.01%, or 0.005% or less of the total weight of the pharmaceutical compositions as impurities arising from the drug substance preparation used to prepare the composition. In other embodiments, the invention provides a pharmaceutical composition having from 0.001%-0.01%, 0.01%-0.1%, or 0.1%-1% of one or more impurities, by weight, wherein the impurities derive from the drug substance preparation used to prepare the pharmaceutical composition. In another embodiment, the invention provides a pharmaceutical composition having from 0.001%-0.01%, 0.005%-0.05%, 0.01%-0.1%, 0.05%-0.5%, 0.1%-1.0%, or 0.5%-5.0%, by weight, of all product-related impurities, process-related impurities, residual solvents, and heavy metals, derived from the drug substance preparation.

In embodiments of this aspect, the invention provides a pharmaceutical composition having a drug substance preparation component containing (R)-(−)-2-(2-fluoro-4-biphenylyl) propionic acid, or a pharmaceutically acceptable salt thereof, as the API, admixed with one or more pharmaceutically acceptable excipients, wherein the weight of the drug substance preparation is more than about 30%, 35%, 40%, 45%, 50%, or 55% of the total weight of the pharmaceutical composition, and further having limited amounts of the impurities arising from the drug substance preparation, as described above. In some of these embodiments, the drug substance preparation component can be about 55% or more, 60% or more, 62% or more, 64% or more, 66% or more, 68% or more, or 70% or more of the total weight of the pharmaceutical composition. In some of these embodiments, the pharmaceutical composition is designed to contain about 200 mg or more, about 300 mg or more, about 400 mg or more, about 500 mg or more, about 600 mg or more, about 700 mg or more, about 800 mg or more of (R)-(−)-2-(2-fluoro-4-biphenylyl) propionic acid as the API in less than about 1600 mg, less than about 1500 mg, less than about 1400 mg, less than about 1300 mg, less than about 1200 mg, less than about 1100 mg, or less than about 1000 mg of pharmaceutical composition.

In still another aspect, the invention provides dosage forms comprising therapeutically effective amounts of (R)-(−)-2-(2-fluoro-4-biphenylyl) propionic acid, or a pharmaceutically acceptable salt thereof, as the API with limited quantities of impurities arising from the drug substance used to prepare the pharmaceutical compositions used to make these dosage forms. These dosage forms can be designed for oral administration, and, in such instances, may take any acceptable form, including tablets, capsules, caplets, powders, and various granular forms. These dosage forms comprise pharmaceutical compositions that, in turn, comprise the drug substance preparations of the invention, which contain (R)-(−)-2-(2-fluoro-4-biphenylyl) propionic acid, or a pharmaceutically acceptable salt thereof, as the API, and limited amounts of impurities, as discussed above. In one set of embodiments, all of the impurities present in these dosage forms represent about 1%, 0.5%, 0.25% 0.1%, 0.05%, 0.025%, 0.01%, 0.005%, 0.0025%, 0.001%, or less of the total weight of the dosage form as impurities (i.e., [sum of weight(s) of impurities derived from the drug substance preparation]/[total weight of dosage form]×100%). In another embodiment, the invention provides dosage forms having from 1-0.1%, 0.1-0.01%, or 0.01-0.001% of the all the impurities arising from the drug substance preparation, as described above. In another embodiment, the invention provides a dosage form having from 1-0.001%, 0.5-0.001%, 0.25-0.001%, 0.1-0.001%, 0.05-0.001%, 0.025-0.001%, or 0.01-0.001% of one or more impurities arising from the drug substance preparation, as described above.

In certain embodiments of this aspect, the invention provides a unit dosage form having (R)-(–)-2-(2-fluoro-4-biphenylyl) propionic acid, or a pharmaceutically acceptable salt thereof, as the API, admixed with one or more pharmaceutically acceptable excipients, wherein the weight of (R)-(–)-2-(2-fluoro-4-biphenylyl) propionic acid, or the pharmaceutically acceptable salt thereof, is more than about 30%, about 35%, about 40%, about 45%, about 50%, about 55%, about 60%, about 65%, about 70% or about 75% of the total weight of the unit dosage form, and further having a limited amounts of impurities arising from the drug substance preparation used to prepare the pharmaceutical composition used to prepare the unit dosage form. In some of these embodiments, (R)-(–)-2-(2-fluoro-4-biphenylyl) propionic acid can be about 57% or more, about 58% or more, about 59% or more, about 60% or more, about 61% or more, about 62% or more, or about 63% or more of the total weight of the unit dosage form. In some of these embodiments, the unit dosage form is manufactured to contain about 200 mg, about 300 mg, about 400 mg, about 500 mg, about 600 mg, about 700 mg, or about 800 mg of (R)-(–)-2-(2-fluoro-4-biphenylyl) propionic acid, as the API.

The unit dosage form of these embodiments can be provided as a unit dosage form specifically suited for oral administration (e.g., a tablet, capsule or caplet). This embodiment of the invention is manufactured using a pharmaceutical composition comprising (R)-(–)-2-(2-fluoro-4-biphenylyl) propionic acid, or a pharmaceutically acceptable salt thereof, as the API, that has from 30% to 90%, 35% to 90%, 40% to 90%, 45% to 90%, 50% to 90%, or 55% to 90%, by weight, (R)-(–)-2-(2-fluoro-4-biphenylyl) propionic acid, or the salt thereof, and from 10% to 45%, by weight, inactive pharmaceutical ingredients, and from 2%-0.001%, by weight, of the impurities arising from the drug substance preparation as described above; wherein all of the percentages, by weight, are of the total weight of the dosage form. In a specific embodiment, the unit dosage form has from 55% to 85% by weight (R)-(–)-2-(2-fluoro-4-biphenylyl) propionic acid and 15%-45% by weight inactive pharmaceutical ingredients. In another specific embodiment, the unit dosage form has from 55% to 75% by weight (R)-(–)-2-(2-fluoro-4-biphenylyl) propionic acid and from 25% to 45% by weight inactive ingredients. In another specific embodiment, the unit dosage form has from 60% to 70% by weight (R)-(–)-2-(2-fluoro-4-biphenylyl) propionic acid and from 30% to 40% by weight inactive pharmaceutical ingredients.

In another embodiment, the invention provides a tablet dosage form having between about 320 and about 480 mg (R)-(–)-2-(2-fluoro-4-biphenylyl) propionic acid, or a pharmaceutically acceptable salt thereof, as the API, wherein the physical dimensions of the tablet, e.g., length, width, volume, etc., are within certain ranges. According to this embodiment, the dosage form also has a limited amount of impurities arising from the drug substance preparation as described above.

In some embodiments of this aspect of the invention, each tablet has (R)-(–)-2-(2-fluoro-4-biphenylyl) propionic acid, or a pharmaceutically acceptable salt thereof, as the API, and limited amount of impurities arising from the drug substance preparation as described above, plus one or more binders, one or more diluents, one or more disintegrants, one or more glidants, one or more lubricants, and if desired, one or more optional ingredients. In one set of embodiments, the tablet dosage form is coated.

In a specific embodiment, the invention provides a tablet dosage form containing about 400 mg (R)-(–)-2-(2-fluoro-4-biphenylyl) propionic acid, or a therapeutically equivalent amount of a pharmaceutically acceptable salt thereof, and having about 30%, 35%, 40%, 45%, 50%, or 55%, or more, by weight, of (R)-(–)-2-(2-fluoro-4-biphenylyl) propionic acid in the tablet, and limited amounts of impurities arising from the drug substance preparations as described above, wherein the total weight of the impurities in the tablet is about 3%, 2%, 1%, 0.5%, or less of the total weight of the tablet. Furthermore, the tablet dosage forms of this embodiment are specifically suited for oral administration.

In a related embodiment, the unit dosage form is a capsule dosage form. In one specific embodiment, the capsule dosage form comprises (R)-(–)-2-(2-fluoro-4-biphenylyl) propionic acid, as the API, and limited amounts of impurities arising from the drug substance preparations used to make the pharmaceutical compositions that go into the capsules, and one or more pharmaceutically acceptable excipients, as described above, as additional components. In one set of embodiments, the capsule dosage form comprises a hard gelatin capsule that contains a pharmaceutical composition of the invention.

In a related set of embodiments, the unit dosage form is a caplet dosage form.

The pharmaceutical compositions and dosage forms of the invention are particularly useful for treating diseases and conditions where relatively large amounts of (R)-(–)-2-(2-fluoro-4-biphenylyl) propionic acid need to be administered to the patient for long periods of time. In some aspects, the invention provides a method of using a unit dosage form, as in any of the embodiments of this aspect of the invention, to treat patients requiring the administration of relatively large amounts of 2-(2-fluoro-4-biphenylyl) propionic acid. This method comprises identifying an individual in need of such treatment, and administering to said individual a therapeutically effective amount of a unit dosage form of the invention. In certain embodiments of this aspect of the invention, the individual in need of treatment has a neurodegenerative disorder. In specific embodiments of the invention, the neurodegenerative disorder is chosen from Alzheimer's disease, dementia, mild cognitive impairment, Parkinson's disease, Huntington's disease, and dementia associated with Down syndrome (i.e., trisomy 21). In certain embodiments of this aspect of the invention, the individual in need of treatment has a disease or condition chosen from prodromal Alzheimer's disease, mild Alzheimer's disease, mild-to-moderate Alzheimer's disease, moderate Alzheimer's disease, moderate-to-severe Alzheimer's disease, severe Alzheimer's disease, dementia, vascular dementia, fronto-temporal dementia, Lewy body dementia, cerebral amyloid angiopathy, beta amyloidosis associated with Down syndrome, and inclusion body mysositis.

In some embodiments of the invention, the individual in need of treatment has a form of Alzheimer's disease which is mild Alzheimer's disease. In other embodiments, the individual in need of treatment does not exhibit the symptoms of Alzheimer's disease, but is at risk for developing Alzheimer's disease. In other embodiments, the individual in need of treatment desires prophylaxis against the onset of Alzheimer's disease, or the symptoms of Alzheimer's disease.

In some embodiments of the invention, single unit dosage forms are administered multiple times daily (e.g., one 800 mg tablet in the morning and one 800 mg tablet in the evening). In other embodiments of the invention, multiple unit dosage forms are administered multiple times daily. For example, two unit dosage forms are administered in the morning and two unit dosage forms are administered in the evening, wherein the unit dosage forms are tablets comprising from about 320 to about 480 mg of (R)-(−)-2-(2-fluoro-4-biphenylyl) propionic acid (or an equivalent molar amount of a pharmaceutically acceptable salt thereof).

In other embodiments of the invention, the individual in need of treatment has or is seeking prevention of cancer. In certain embodiments, such individual has a cancer chosen from brain, lung, liver, spleen, kidney, lymph node, small intestine, pancreas, blood cell, colon, stomach, breast, endometrial, prostate, testicle, ovary, skin, and head and neck cancer, esophagus, and bone marrow cancer. In one embodiment, the individual in need of treatment has prostate cancer. Skilled artisans are capable of identifying individuals in need of such treatment.

In summary, the invention provides a drug substance preparation, pharmaceutical composition, or dosage form containing (R)-(−)-2-(2-fluoro-4-biphenylyl) propionic acid, or a pharmaceutically acceptable salt thereof, as the API, and about 5%, 4%, 3%, 2%, 1%, 0.5%, or 0.25% or less (of the total weight of a particular composition) of all of the product-related impurities, process-related impurities, residual solvents and heavy metals, as defined below. In another embodiment, the invention provides a drug substance preparation, pharmaceutical composition, or dosage form containing (R)-(−)-2-(2-fluoro-4-biphenylyl) propionic acid, or a pharmaceutically acceptable salt thereof, as the API, and about 0.005%, 0.01%, 0.03%, 0.05%, 0.07%, 0.08%, 0.09% or 0.1% or more (of the total weight of a particular composition) of one or more of the product-related impurities, process-related impurities, residual solvents and heavy metals, as defined below. In a specific embodiment, the invention provides a drug substance preparation, pharmaceutical composition, or dosage form having from 5-0.5%, 1-0.1%, 0.5-0.05%, 0.1-0.01%, 0.05-0.005%, or 0.01-0.001% of one or more of the product-related impurities, process-related impurities, residual solvents and heavy metals, as defined below. In another specific embodiment, the invention provides a drug substance preparation, pharmaceutical composition, or dosage form having from 5-0.5%, 1-0.1%, 0.5-0.05%, 0.1-0.01%, 0.05-0.005%, or 0.01-0.001% of all of the product-related impurities, process-related impurities, residual solvents and heavy metals, as defined below.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, examples of suitable methods and materials are described below. In case of conflict, the present specification, including definitions, will control. In addition, the materials, methods, and examples are illustrative only and are not intended to be limiting.

Other features and advantages of the invention will be apparent from the following detailed description, and from the claims.

DETAILED DESCRIPTION OF THE INVENTION

The drug substance preparations, pharmaceutical compositions, and dosage forms of the invention all contain (R)-(−)-2-(2-fluoro-4-biphenylyl) propionic acid as the active pharmaceutical ingredient (API). (R)-(−)-2-(2-fluoro-4-biphenylyl) propionic acid is also known as (−)-(2R)-2-(2-fluorobiphenyl-4-yl)propanionic acid, 1,1'-biphenyl]-4-acetic acid, 2-fluoro-α-methyl-,(αR), and tarenflurbil (USAN and INN name), and has been given a CAS Registry® number of 51543-40-9. (R)-(−)-2-(2-fluoro-4-biphenylyl) propionic acid is the "R" enantiomer of flurbiprofen ((R,S)-2-(2-fluoro-4-biphenylyl) propionic acid). (R)-(−)-2-(2-fluoro-4-biphenylyl) propionic acid can be obtained by resolving racemic flurbiprofen into it's separate enantiomeric forms, or through enantioselective or enantiospecific syntheses. The R-enantiomer of flurbiprofen ((R)-(−)-2-(2-fluoro-4-biphenylyl) propionic acid), or a particular desired enantiomeric excess of (R)-(−)-2-(2-fluoro-4-biphenylyl) propionic acid, can be obtained by resolving the racemic flurbiprofen according to known methods, as noted herein.

The R-enantiomer of flurbiprofen ((R)-(−)-2-(2-fluoro-4-biphenylyl) propionic acid), is commercially available (e.g., Caymen Chemical, Ann Arbor, Mich.). However, to the best of our knowledge, and with the possible exception of (S)-(+)-2-(2-fluoro-4-biphenylyl) propionic acid, the identities and amounts of product-related and process-related impurities found in preparations of (R)-(−)-2-(2-fluoro-4-biphenylyl) propionic acid, have never been described, and never held to specifically-defined limits.

Methods of resolving (R)-(−)-2-(2-fluoro-4-biphenylyl) propionic acid from racemic flurbiprofen are disclosed in U.S. Pat. No. 5,599,969 of Hardy et al. (assigned to The Boots Company PLC (Nottingham, GB)). These methods, which have been adapted to the present invention, and are described in detail below, involve reacting racemic flurbiprofen with α-methylbenzylamine to form an isolatable salt of (R)-(−)-2-(2-fluoro-4-biphenylyl) propionic acid. U.S. Pat. No. 4,209,638 of Nicholson and Tantum (also assigned to The Boots Company PLC (Nottingham, GB)) discloses a process for resolving 2-arylpropionic acids, which include flurbiprofen, by mixing the racemate with a chiral organic nitrogenous base under certain conditions followed by recovery and separation of the diastereomeric salts. Other patents disclosing processes for resolving racemic arylpropionic acids include U.S. Pat. No. 4,983,765 (assigned to PAZ Arzneimittel-Entwicklungsgesellschaft mbH (Frankfurt am Main, Del.)); U.S. Pat. No. 5,015,764 (assigned to Ethyl Corporation (Richmond, Va.)); U.S. Pat. No. 5,235,100 (also assigned to Ethyl Corporation (Richmond, Va.)); U.S. Pat. No. 5,574,183 (assigned to Albemarle Corporation (Richmond, Va.); and U.S. Pat. No. 5,510,519 (assigned to Sumitomo Chemical Company, Limited (Osaka, JP)).

Importantly, the inventors have discovered drug substance preparations having (R)-(−)-2-(2-fluoro-4-biphenylyl) propionic acid as the API, and containing substantially limited amounts of specific product-related and process-related impurities, residual solvents and heavy metals. The inventive drug substance preparations allow for the production of pharmaceutical compositions that further allow for the production of dosage forms having (R)-(−)-2-(2-fluoro-4-biphenylyl) propionic acid (or a pharmaceutically acceptable salt thereof) as the API, and substantially limited quantities of specific impurities. These pharmaceutical compositions and dosage forms are particularly well suited for use in treating (and/or preventing) conditions or diseases, like, for instance, Alzheimer's disease, that require the dosing of high levels of (R)-(−)-2-(2-fluoro-4-biphenylyl) propionic acid for extended periods of time. Under such dosing regimes, it is important to use drug substance preparations of high purity, and with substantially limited amounts of specific product- and process-related impurities, residual solvents, and heavy metals, in the preparation of pharmaceutical compositions and dosage forms in order to minimize the exposure of patients to these impurities, and thereby minimize the likelihood of any deleterious effects that may be caused by such impurities.

Consequently, the inventors have also discovered pharmaceutical compositions containing these drug substance preparations as the source of the API, that allow for the production of oral dosage forms such as, for example, tablets having 200 mg or more of API and substantially limited amounts of specific impurities. These pharmaceutical compositions, and the dosage forms comprising them, have desirable physical, mechanical and manufacturing properties, requisite stability, excellent dissolution profiles, and therapeutically desirable pharmacokinetic profiles.

The invention relates to drug substance preparations having (R)-(−)-2-(2-fluoro-4-biphenylyl) propionic acid, or a pharmaceutically acceptable salt thereof, as the API, and having substantially limited amounts of specific impurities associated with the synthesis and purification of the API. The invention further relates to pharmaceutical compositions made from these drug substance preparations, and dosage forms or drug products made from these pharmaceutical compositions.

The invention encompasses pharmaceutical compositions suitable for oral administration, and pharmaceutical dosage forms designed for oral administration, that provide physical, pharmaceutical, pharmacokinetic, and therapeutic characteristics particularly useful in treating Alzheimer's disease, and in slowing or preventing the progression of symptoms of Alzheimer's disease, as well as other disorders that benefit from the administration of large quantities of the API over extended periods of time. Specifically, these pharmaceutical compositions and dosage forms are designed to be used in the treatment of patients who are in need of such treatment, and who will require doses of the API, for example, on the order of at least about 800 mg API, twice daily for extended periods of time, for example, for 5, 10, 20, or more, years.

The pharmaceutical compositions and the dosage forms of the invention are formulated with (R)-(−)-2-(2-fluoro-4-biphenylyl) propionic acid, or a pharmaceutically acceptable salt thereof, as the API in the drug substance preparation, and one or more pharmaceutically acceptable excipients (inactive pharmaceutical ingredients), in admixture with the drug substance preparation. The pharmaceutical compositions and dosage forms of the invention are specifically formulated for administration of the API to patients in need of such treatment, and, in particular embodiments, are formulated for oral administration (e.g., a tablet dosage form). The (R)-(−)-2-(2-fluoro-4-biphenylyl) propionic acid containing compositions and dosage forms of the invention are designed to be used in methods for treating or preventing (e.g., delaying the onset of one or more symptoms of a disease), neurodegenerative disorders such as Alzheimer's disease, or neoplastic diseases such as prostate cancer.

DEFINITIONS

The term "(R)-(−)-2-(2-fluoro-4-biphenylyl) propionic acid," as used herein, refers to the free acid form of (R)-(−)-2-(2-fluoro-4-biphenylyl) propionic acid, and to pharmaceutically acceptable salt forms thereof. Where pharmaceutically acceptable salts are employed in the various aspects and embodiments of the invention, the specific amounts and ranges of salts to be used are ideally the amounts and ranges that are bioequivalent to those indicated for the free acid. That is to say, if a pharmaceutically acceptable salt is used in a drug substance preparation, composition, dosage form, or drug product of the invention, it should be used in the amount necessary to provide a therapeutic effect equivalent to that obtained with the free acid form of (R)-(−)-2-(2-fluoro-4-biphenylyl) propionic acid (i.e., a "therapeutically equivalent" amount of the pharmaceutically acceptable salt). In most instances, this simply means using a molar equivalent amount of the pharmaceutically acceptable salt in place of the specified amount of the free acid form used in the particular embodiment.

As used herein, the term "dose" or "dosage" refers to the amount of active pharmaceutical ingredient that an individual takes or is administered at one time. For example, an 800 mg (R)-(−)-2-(2-fluoro-4-biphenylyl) propionic acid dose refers to, in the case of a twice-daily dosage regimen, a situation where, for example, the individual takes, or is administered, 800 mg (R)-(−)-2-(2-fluoro-4-biphenylyl) propionic acid in the morning and 800 mg (R)-(−)-2-(2-fluoro-4-biphenylyl) propionic acid in the evening. The 800 mg (R)-(−)-2-(2-fluoro-4-biphenylyl) propionic acid dose can be a single unit or can be divided into two or more dosage units, e.g., two 400 mg (R)-(−)-2-(2-fluoro-4-biphenylyl) propionic acid tablets or two 400 mg (R)-(−)-2-(2-fluoro-4-biphenylyl) propionic acid capsules. As used herein, the term "unit dosage form" refers to a physically discrete unit, such as a tablet or capsule suitable as a unitary dosage for a human patient. Each unit contains a predetermined quantity of (R)-(−)-2-(2-fluoro-4-biphenylyl) propionic acid that was discovered to produce a desired pharmacokinetic profile which yields the desired therapeutic effect.

The term "active pharmaceutical ingredient," or "API," as used herein in the context of the drug substance preparations, pharmaceutical compositions, and dosage forms or drug products of the invention, refers to the free acid form of (R)-(−)-2-(2-fluoro-4-biphenylyl) propionic acid, or

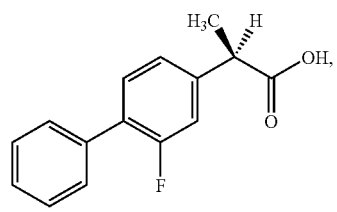

and to pharmaceutically acceptable salt forms thereof.

As used herein, the terms "drug substance" and "drug substance preparation," refers to the API-containing material that is used to formulate, along with excipients, the pharmaceutical compositions, dosage forms, and drug products of the invention. It is composed of the API, and limited quantities of specific product-related impurities, process-related impurities, residual solvents, and heavy metals.

The term "excipient," as used herein, refers to those components of a pharmaceutical composition, dosage form, or drug product, other than the drug substance, that are intentionally included in the composition or formulation to either facilitate manufacture, enhance stability, control the release of the API from the drug product, assist in product identification, or enhance any other product characteristics, including, for example, the pharmacokinetics of the drug product. Generally, excipients may be thought of as the "inactive ingredients" of the pharmaceutical composition, dosage form, or drug product, in the sense that they exert no direct therapeutic effect. However, excipients can have a significant effect on the pharmacokinetic characteristics of pharmaceutical compositions, dosage forms, or drug products containing the API, by influencing such parameters as dissolution, and release of the API.

As used herein, the term "pharmaceutical composition" is used to refer to compositions of matter comprising the drug substance and one or more pharmaceutically acceptable excipients. Additionally, these terms are meant to refer to compositions of matter (containing the drug substance and one or more excipients) that are used to prepare drug products or dosage forms, along with one or more additional excipients.

As used herein, the terms "drug product," "dosage form," or "finished product" are used interchangeably to refer to a finished pharmaceutical product or medicament that is suitable for administration to a human patient. The drug product or dosage form comprises the drug substance and pharmaceutically acceptable excipients, and can also be thought of as comprising a pharmaceutical composition in combination with one or more additional excipients. One example of a drug product or dosage form is a "tablet dosage form," or "tablet," which is formulated and manufactured for the gastrointestinal administration of the API by an oral route (i.e., oral administration).

The term "impurity," as used herein, refers to any component present in the drug substance (or a drug substance preparation), a pharmaceutical composition thereof, or a drug product or dosage form thereof, that is neither the API nor an excipient. For the sake of this application, the term "impurity" generally refers to impurities arising from, or contained in, the drug substance, or a drug substance preparation. Consequently, the term "impurity" comprises product-related impurities, process-related impurities, residual solvents, and heavy metals, which are found in the drug substance or drug substance preparations.

As used herein, the term "product-related impurities" refers to organic chemicals that are structurally similar to the API, that are found in drug substance preparations, but that do not have properties comparable to those of the API with respect to activity, efficacy, and safety. Product-related impurities can also include "degradants," which are products of the degradation of the API. The term "product-related impurities" also encompasses enantiomeric impurities. In the instant invention the sole enantiomeric impurity is:

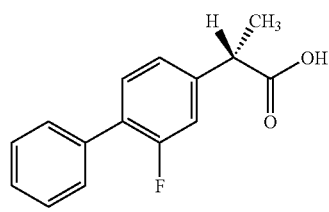 [SMILES: C[C@H](C(=O)O)c1ccc(-c2ccccc2)c(F)c1]

(S)-(+)-2-(2-fluoro-4-biphenylyl) propionic acid, which is also known as (S)-flurbiprofen. However, given that this enantiomeric impurity is of particular concern in the drug substance preparations, pharmaceutical compositions, and dosage forms of the invention, it will generally be considered apart from, or in addition to, all other product-related impurities.

Specific examples of "product-related impurities" besides (S)-(+)-2-(2-fluoro-4-biphenylyl) propionic acid found in the drug substance preparations, pharmaceutical compositions and dosage forms of the instant invention can include:

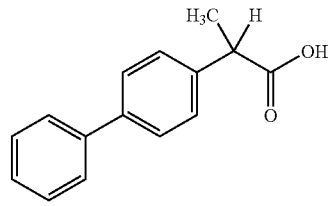 [SMILES: CC(C(=O)O)c1ccc(-c2ccccc2)cc1]

2-(4-biphenylyl) propionic acid;

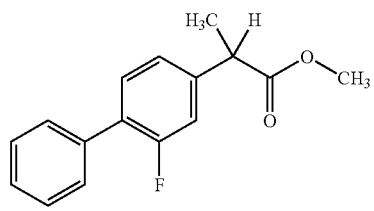 [SMILES: COC(=O)C(C)c1ccc(-c2ccccc2)c(F)c1]

methyl (2-(2-fluoro-4-biphenylyl)) propionate;

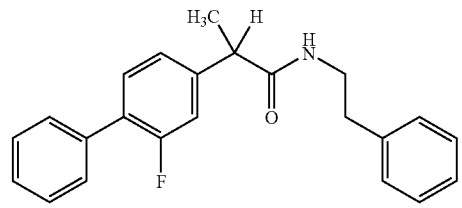 [SMILES: CC(C(=O)NCCc1ccccc1)c1ccc(-c2ccccc2)c(F)c1]

1-phenylethyl-(2-2(fluorobiphenyl-4-yl)) propionamide; and

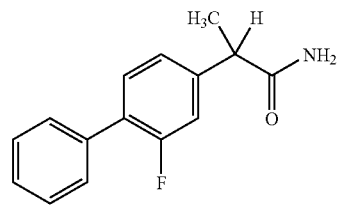 [SMILES: CC(C(N)=O)c1ccc(-c2ccccc2)c(F)c1]

2-(2-fluorobiphenyl-4-yl) propionamide.

The term "process-related impurities," as used herein, refers to impurities other than product-related impurities, which derive from the process used to manufacture the drug substance preparation. Process-related impurities commonly found in drug substance preparations include residual solvents, catalysts and other compounds used in the synthesis of the API, heavy metals, and compounds used during the purification the API.

Specific examples of "process-related impurities" in the instant invention include the solvents toluene, methanol and n-heptane, heavy metals (measured as ppm Pb), and the chiral crystallization agent (R)-(+)-α-methylbenzylamine:

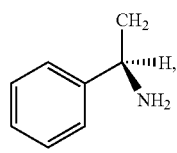

which is also known as (R)-(+)-1-phenylethylamine.

Drug Substance and Drug Substance Preparations

A method for preparing the drug substance of the invention is provided in Example 1, below. This method can generally be divided into two distinct parts. In the first part of the method, racemic flurbiprofen (i.e., (R,S)-2-(2-fluoro-4-biphenylyl) propionic acid) is produced using methods known in the art. These methods encompass, for example, those synthetic methods described in U.S. Pat. Nos. 3,755,427 and 3,959,364, both of which are incorporated by reference herein in their entirety. In the second part, racemic flurbiprofen is subjected to a chiral resolution process that involves the crystallization and recovery of (R)-(−)-2-(2-fluoro-4-biphenylyl) propionic acid as a chiral salt. This process, which is based upon the method described in U.S. Pat. No. 5,599,969 (which is also incorporated by reference herein in its entirety), is more fully described in Example 1, below.

Briefly, the resolution process used to create the drug substance preparations of the present invention, involves the controlled addition of a specific molar amount of the enantiopure optical resolution agent (R)-(+)-α-methylbenzylamine, to a specific molar amount of racemic flurbiprofen that is dissolved in a defined volume of a defined mixture of toluene and methanol, under conditions that facilitate the formation of the (R)-(+)-α-methylbenzylamine salts of both (R)-(−)- and (S)-(+)-2-(2-fluoro-4-biphenylyl) propionic acid. The resulting solution, which is prepared to produce a specific level of supersaturation, is then maintained under appropriate temperature and mixing conditions to allow for the spontaneous formation of crystals of the (R)-(+)-α-methylbenzylamine salt of (R)-(−)-2-(2-fluoro-4-biphenylyl) propionic acid. Crystal nucleation and growth are controlled by carefully controlling the temperature, concentration and mixing of the crystallization solution. Crystal particle size distribution is optimized through a thermal ripening step, as described in the example. The resulting crystals of the (R)-(+)-α-methylbenzylamine salt of (R)-(−)-2-(2-fluoro-4-biphenylyl) propionic acid are isolated by filtration. Following initial isolation and washing, the salt crystals are resuspended and recrystallized once more from a defined mixture of toluene and methanol, under a second carefully controlled crystallization step. The recrystallized (R)-(+)-α-methylbenzylamine:(R)-(−)-2-(2-fluoro-4-biphenylyl) propionic acid salt crystals, are isolated and washed, and resuspended again. Following resuspension, (R)-(−)-2-(2-fluoro-4-biphenylyl) propionic acid and (R)-(+)-α-methylbenzylamine are liberated from the (R)-(+)-α-methylbenzylamine salt of (R)-(−)-2-(2-fluoro-4-biphenylyl) propionic acid by a metathesis reaction driven by the addition of a defined amount of hydrochloric acid. The liberated (R)-(−)-2-(2-fluoro-4-biphenylyl) propionic acid is separated from the liberated (R)-(+)-α-methylbenzylamine by a selective extraction, and the (R)-(−)-2-(2-fluoro-4-biphenylyl) propionic acid is crystallized under carefully controlled conditions, and subsequently isolated by filtration. The isolated (R)-(−)-2-(2-fluoro-4-biphenylyl) propionic acid crystals are extensively washed with n-heptane, and the n-heptane is remove under vacuum to yield the drug substance of the present invention.

Thus in one aspect, the invention provides methods to resolve racemic flurbiprofen (i.e., (R,S)-2-(2-fluoro-4-biphenylyl) propionic acid) using chiral crystallization, in order to purify the API, (R)-(−)-2-(2-fluoro-4-biphenylyl) propionic acid, and produce drug substance preparations containing the limited amounts of product-related impurities, process-related impurities, residual solvents and heavy metals, as described below.

Impurities in Drug Substance Preparations

All drug substance preparations in which the API is a small organic molecule (such as (R)-(−)-2-(2-fluoro-4-biphenylyl) propionic acid) that is synthesized from smaller, more readily-available starting materials, and isolated from organic solvents, can be expected to contain impurities. Generally, the types of impurities seen in such drug substance preparations are dictated by the synthetic route and specific processes used to prepare the API. Certainly, the amounts of impurities observed in drug substance preparations can be reduced or controlled by steps taken at various points during the synthesis and purification of the API.

In the present invention, drug substance preparations are provided that contain (R)-(−)-2-(2-fluoro-4-biphenylyl) propionic acid, or a pharmaceutically acceptable salt thereof, as the API. These drug substance preparations are made using the methods provided that substantially reduce the amounts of impurities present, and limit the amounts impurities that remain. Hence, the drug substance preparations of the present invention contain limited amount of specific impurities, the identity and quantity of which have been determined, and are described herein.

As noted above, impurities that occur in the (R)-(−)-2-(2-fluoro-4-biphenylyl) propionic acid-containing drug substance preparations of the present invention include product-related impurities, process-related impurities, residual solvents and heavy metals. Product-related impurities known to occur within the drug substance preparations of the present invention include the enantiomeric impurity (S)-(+)-2-(2-fluoro-4-biphenylyl) propionic acid (i.e., (S)-flurbiprofen), as well as 2-(4-biphenylyl) propionic acid and methyl (2-(2-fluoro-4-biphenylyl)) propionate, and occasionally include 1-phenylethyl-(2-2(fluorobiphenyl-4-yl)) propionamide and 2-(2-fluorobiphenyl-4-yl) propionamide. Process-related impurities known to occur within the drug substance preparations of the present invention include the chiral crystallization agent (R)-(+)-α-methylbenzylamine, as well as residual solvents, including toluene, methanol and n-heptane, and trace amounts of heavy metals. Table 3, in Example 4, below, provides the amounts of specific, selected impurities found in two exemplary batches of drug substance made according to the method disclosed in Example 1.

In view of the above, a first aspect of the present invention provides drug substance preparations containing (R)-(−)-2-(2-fluoro-4-biphenylyl) propionic acid, or a pharmaceutically acceptable salt thereof, as the API, and limited amounts of specific product-related impurities, process-related impurities, residual solvents and heavy metals. In one embodiment of this aspect, all of the impurities present in these drug substance preparations are limited to about 5%, 4%, 3%, 2%, 1%, or less of the total weight of the drug substance preparation (i.e., [sum of weight(s) of one or more impurities]/[total weight of drug substance preparation]×100% is less than about 5%, 4%, 3%, 2%, 1%, or less). In another embodiment, the invention provides a drug substance preparation containing (R)-(−)-2-(2-fluoro-4-biphenylyl) propionic acid, or a pharmaceutically acceptable salt thereof, as the API, and about 2%, 1%, 0.5%, 0.25%, 0.1%, 0.05%, 0.025%, 0.01%, 0.005%, 0.0025%, or 0.001% of the total weight of the drug substance preparation as product-related impurities. In another embodiment, the invention provides a drug substance preparation having from 0.001%-0.01%, 0.005%-0.05%, 0.01%-0.1%, 0.05%-0.5%, or 0.1%-1%, of any one specific impurity, by weight. In another embodiment, the invention provides a drug substance preparation having from 0.001%-0.01%, 0.005%-0.05%, 0.01%-0.1%, 0.05%-0.5%, 0.1%-1%, or 0.5%-5%, by weight, of the specific product-related impurities, process-related impurities, residual solvents and heavy metals identified herein.

In certain embodiments, the present invention comprises drug substance preparations containing (R)-(−)-2-(2-fluoro-4-biphenylyl) propionic acid as the API, and limited amounts of product-related impurities. In these embodiments, the product-related impurities that are present in limited amounts include the enantiomeric impurity (S)-(+)-2-(2-fluoro-4-biphenylyl) propionic acid, which is also know as (S)-flurbiprofen, 2-(4-biphenylyl) propionic acid, and methyl (2-(2-fluoro-4-biphenylyl))propionate. In specific embodiments, the present invention comprises drug substance preparations wherein the amounts of 2-(4-biphenylyl) propionic acid, as well as the enantiomeric impurity (S)-(+)-2-(2-fluoro-4-biphenylyl) propionic acid, are limited below certain maximum levels. In other specific embodiments, the present invention comprises drug substance preparations wherein the amounts of both 2-(4-biphenylyl) propionic acid and methyl (2-(2-fluoro-4-biphenylyl))propionate, as well as the enantiomeric impurity (S)-(+)-2-(2-fluoro-4-biphenylyl) propionic acid, are limited below certain maximum levels.

In certain embodiments, the present invention comprises drug substance preparations wherein, in addition to the amounts of one or two known product-related impurities, as well as the enantiomeric impurity (S)-(+)-2-(2-fluoro-4-biphenylyl) propionic acid, being limited below certain maximum levels, the amounts of specific process-related impurities are also limited below certain maximum levels. In these embodiments, the principle process-related impurity that is limited below certain maximum levels is (R)-(+)-α-methylbenzylamine, which is also known as (R)-(+)-1-phenylethylamine, and which is used to resolve and isolate (R)-(−)-2-(2-fluoro-4-biphenylyl) propionic acid from racemic flurbiprofen (i.e., (R,S)-2-(2-fluoro-4-biphenylyl) propionic acid). In further embodiments, additional process-related impurities that are limited below certain maximum levels include residual solvents, and/or heavy metals. In these embodiments, the residual solvents to be limited include toluene, methanol, and n-heptane.

In a preferred embodiment of this aspect of the invention, the present invention comprises drug substance preparations containing: (R)-(−)-2-(2-fluoro-4-biphenylyl) propionic acid as the API; limited amounts of three product-related impurities, including the enantiomeric impurity (S)-(+)-2-(2-fluoro-4-biphenylyl) propionic acid, 2-(4-biphenylyl) propionic acid, and methyl (2-(2-fluoro-4-biphenylyl))propionate; limited amounts of the process-related impurity (R)-(+)-α-methylbenzylamine; and limited amounts of residual solvents and heavy metals.

Selected Drug Substance Preparation Impurities

As demonstrated in Example 3, below, select product-related impurities detected in an exemplary batch of (R)-(−)-2-(2-fluoro-4-biphenylyl) propionic acid-containing drug substance preparations include, for example, 2-(4-biphenylyl) propionic acid and methyl (2-(2-fluoro-4-biphenylyl)) propionate, in addition to the S-enantiomer of flurbiprofen, or (S)-(+)-2-(2-fluoro-4-biphenylyl) propionic acid. Similarly, process-related impurities detected in an exemplary batch of (R)-(−)-2-(2-fluoro-4-biphenylyl) propionic acid-containing drug substance preparations include, for example, (R)-(+)-α-methylbenzylamine, residual toluene, residual methanol, and residual n-heptane, as well as trace amounts of heavy metals. Importantly, the inventive drug substance preparations containing limited amount of the above-listed impurities allow for the production of pharmaceutical compositions and dosage forms having therapeutically effective amounts of (R)-(−)-2-(2-fluoro-4-biphenylyl) propionic acid (or therapeutically equivalent amounts of a pharmaceutically acceptable salt thereof), but substantially limited quantities of impurities. Thus, the inventors have discovered methods of manufacturing (R)-(−)-2-(2-fluoro-4-biphenylyl) propionic acid-containing drug substance that contains substantially limited amounts of specific impurities, which is subsequently used to prepare the pharmaceutical compositions, and, ultimately, the dosage forms of the present invention.

When these impurities are considered separately in the context of drug substance preparations, one arrives at the following embodiments of this aspect of the invention.

In some embodiments, the (R)-(−)-2-(2-fluoro-4-biphenylyl) propionic acid-containing drug substance preparations used in the pharmaceutical compositions and dosage forms of the invention has less than about 1.0%, 0.9%, 0.8%, 0.7%, 0.6%, 0.5%, 0.4%, 0.3%, 0.2%, or 0.1%, by weight, 2-(4-biphenylyl) propionic acid.

In some embodiments, the (R)-(−)-2-(2-fluoro-4-biphenylyl) propionic acid-containing drug substance preparations used in the pharmaceutical compositions and dosage forms of the invention has less than about 0.2%, 0.18%, 0.16%, 0.14%, 0.12%, 0.1%, 0.09%, 0.08%, 0.07%, or 0.06%, by weight, methyl (2-(2-fluoro-4-biphenylyl))propionate.

In some embodiments, the (R)-(−)-2-(2-fluoro-4-biphenylyl) propionic acid-containing drug substance preparations used in the pharmaceutical compositions and dosage forms of the invention has less than about 0.2%, 0.18%, 0.16%, 0.14%, 0.12%, 0.1%, 0.09%, 0.08%, 0.07%, or 0.06%, by weight, 1-phenylethyl-(2-2(fluorobiphenyl-4-yl)) propionamide.

In some embodiments, the (R)-(−)-2-(2-fluoro-4-biphenylyl) propionic acid-containing drug substance preparations used in the pharmaceutical compositions and dosage forms of the invention has less than about 0.2%, 0.18%, 0.16%, 0.14%, 0.12%, 0.1%, 0.09%, 0.08%, 0.07%, or 0.06%, by weight, 2-(2-fluorobiphenyl-4-yl) propionamide.

In some embodiments, the (R)-(−)-2-(2-fluoro-4-biphenylyl) propionic acid-containing drug substance preparations used in the pharmaceutical compositions and dosage forms of the invention has an enantiomeric excess of (R)-(−)-2-(2-fluoro-4-biphenylyl) propionic acid of about 95%, 98%, 99%, 99.1%, 99.2%, 99.3%, 99.4%, 99.5%, 99.6%, 99.7%, 99.8%, or 99.9% over the S-enantiomer of flurbiprofen, namely (S)-(+)-2-(2-fluoro-4-biphenylyl) propionic acid. Respectively, in these embodiments, the (R)-(−)-2-(2-fluoro-4-biphenylyl) propionic acid-containing drug substance preparations used in the pharmaceutical compositions and dosage forms of the invention has not more than about 3%, 2%, 1%, 0.5%, 0.45%, 0.4%, 0.35%, 0.3%, 0.25%, 0.2%, 0.15%, 0.1%, or 0.05%, or less, by weight, (S)-(+)-2-(2-fluoro-4-biphenylyl) propionic acid.

In some embodiments, the (R)-(−)-2-(2-fluoro-4-biphenylyl) propionic acid-containing drug substance preparations used in the pharmaceutical compositions and dosage forms of the invention has not more than about 200 ppm, 100 ppm, 50 ppm, 25 ppm, 10 ppm, or 5 ppm, or less, of the process-related impurity, (R)-(+)-α-methylbenzylamine.

In some embodiments, the (R)-(−)-2-(2-fluoro-4-biphenylyl) propionic acid-containing drug substance preparations used in the pharmaceutical compositions and dosage forms of the invention has less than about 900 ppm, 800 ppm, 700 ppm, 600 ppm, 500 ppm, 400 ppm, 300 ppm, 200 ppm, or 100 ppm toluene.

In some embodiments, the (R)-(−)-2-(2-fluoro-4-biphenylyl) propionic acid-containing drug substance preparations used in the pharmaceutical compositions and dosage forms of the invention has less than about 0.5%, 0.4%, 0.3%, 0.2%, 0.1%, 0.05%, or 0.025%, by weight, methanol.

In some embodiments, the (R)-(−)-2-(2-fluoro-4-biphenylyl) propionic acid-containing drug substance preparations used in the pharmaceutical compositions and dosage forms of the invention has less than about 0.5%, 0.4%, 0.3%, 0.2%, 0.1%, 0.05%, or 0.025%, by weight, n-heptane.

In some embodiments, the (R)-(−)-2-(2-fluoro-4-biphenylyl) propionic acid acid-containing drug substance preparations used in the pharmaceutical compositions and dosage forms of the invention has less than about 100 ppm, 50 ppm, 25 ppm, 10 ppm, 8 ppm, 6 ppm, 4 ppm, 2 ppm, or 1 ppm heavy metals (calculated as Pb), as determined by the Ph Eur, USP method.

In light of the above, the invention provides drug substance preparations comprising (R)-(−)-2-(2-fluoro-4-biphenylyl) propionic acid, or a pharmaceutically acceptable salt thereof, as the active pharmaceutical ingredient, and one or more of the above-identified impurities, in the above-identified amounts.

In a preferred embodiment, the invention provides a drug substance preparations comprising (R)-(−)-2-(2-fluoro-4-biphenylyl) propionic acid, or a pharmaceutically acceptable salt thereof, as the active pharmaceutical ingredient, and between about 0.001% and about 3%, by weight, product-related impurities, wherein said product-related impurities comprise not more than about 0.5%, by weight, 2-(4-biphenylyl) propionic acid and not more than 2%, by weight, of the enantiomeric impurity (S)-(+)-2-(2-fluoro-4-biphenylyl) propionic acid, or a salt thereof.

In another preferred embodiment, the invention provides a drug substance preparation comprising:

(1) (R)-(−)-2-(2-fluoro-4-biphenylyl) propionic acid, or a pharmaceutically acceptable salt thereof, as the active pharmaceutical ingredient;

(2) between about 0.001% and about 2%, by weight, product-related impurities, wherein said product-related impurities comprise:

(a) not more than about 0.5%, by weight, 2-(4-biphenylyl) propionic acid, (b) not more than about 0.1%, by weight, methyl (2-(2-fluoro-4-biphenylyl)) propionate, and (c) not more than about 1.0%, by weight, of the enantiomeric impurity (S)-(+)-2-(2-fluoro-4-biphenylyl) propionic acid, or a salt thereof;

(3) not more than about 50 ppm of the process-related impurity, (R)-(+)-α-methylbenzylamine;

(4) not more than about 900 ppm of toluene, not more than about 0.3%, by weight, methanol, and not more than about 0.3%, by weight, n-heptane; and (5) not more than about 10 ppm heavy metals.

Additionally, in certain embodiments, the (R)-(−)-2-(2-fluoro-4-biphenylyl) propionic acid-containing drug substance preparations used in the pharmaceutical compositions and dosage forms of the invention has less than about 0.2%, 0.18%, 0.16%, 0.14%, 0.12%, 0.1%, 0.09%, 0.08%, 0.07%, or 0.06%, by weight, of any other specifically named impurity.

In other embodiments, the (R)-(−)-2-(2-fluoro-4-biphenylyl) propionic acid-containing drug substance preparations used in the pharmaceutical compositions and dosage forms of the invention has less than about 0.2%, 0.18%, 0.16%, 0.14%, 0.12%, 0.1%, 0.09%, 0.08%, 0.07%, or 0.06%, by weight, unidentified impurities.

In other embodiments, the (R)-(−)-2-(2-fluoro-4-biphenylyl) propionic acid-containing drug substance preparations used in the pharmaceutical compositions and dosage forms of the invention has no detectable impurities. Alternatively, the impurities are detectable but are less than about 0.01% of the weight of the drug substance preparation.

In other embodiments, the (R)-(−)-2-(2-fluoro-4-biphenylyl) propionic acid-containing drug substance preparations used in the pharmaceutical compositions and dosage forms of the invention has less than about 0.2%, 0.18%, 0.16%, 0.14%, 0.12%, 0.1%, 0.09%, 0.08%, 0.07%, or 0.06%, by weight, residue upon ignition.

In other embodiments, the (R)-(−)-2-(2-fluoro-4-biphenylyl) propionic acid acid-containing drug substance preparations used in the pharmaceutical compositions and dosage forms of the invention has less than about 1.0%, 0.9%, 0.8%, 0.7%, 0.6%, 0.5%, 0.4%, 0.3%, 0.2%, or 0.1% loss of weight on drying for 3 or more hours at 60° C. with pressure not exceeding 5 mm of Hg over phosphorous pentoxide.

Pharmaceutical Compositions

In another aspect, the present invention provides pharmaceutical compositions comprising the drug substance preparations described above.

As described above, (R)-(−)-2-(2-fluoro-4-biphenylyl) propionic acid-containing drug substance preparations include specific product-related impurities, process-related impurities, residual solvents and trace amounts of heavy metals. Since these drug substance preparations are used to prepare the pharmaceutical compositions of the invention, the pharmaceutical compositions of the invention also include the product-related impurities, 2-(4-biphenylyl) propionic acid and methyl (2-(2-fluoro-4-biphenylyl)) propionate, in addition to the S-enantiomer of flurbiprofen, namely (S)-(+)-2-(2-fluoro-4-biphenylyl) propionic acid. Similarly, the pharmaceutical compositions of the invention also include the process-related impurities such as, for example, (R)-(+)-α-methylbenzylamine, residual toluene, residual methanol, and residual n-heptane, as well as trace amounts of heavy metals.

Consequently, in embodiments of this aspect of the invention, the pharmaceutical compositions of the invention comprise (R)-(−)-2-(2-fluoro-4-biphenylyl) propionic acid as the API, and further comprise limited quantities of product-related impurities, process-related impurities, residual solvents and heavy metals. In these embodiments, the present invention provides pharmaceutical compositions in which all of the impurities deriving from the drug substance preparations of the invention represent about 2%, 1%, 0.5%, 0.25% 0.1%, 0.05%, 0.025%, 0.01%, or less of the total weight of the pharmaceutical composition (i.e., [sum of weight(s) of impurities deriving from the drug substance preparation]/[total weight of pharmaceutical composition]×100%). In certain embodiments of this aspect, the invention provides pharmaceutical compositions containing (R)-(−)-2-(2-fluoro-4-biphenylyl) propionic acid, or a pharmaceutically acceptable salt thereof, as the API, and about 0.5%, 0.25%, 0.1%, 0.05%, 0.025%, 0.01%, or 0.005% or less of the total weight of the pharmaceutical compositions as impurities arising from the drug substance preparation used to prepare the composition. In other embodiments, the invention provides a pharmaceutical composition having from 0.001%-0.01%, 0.01%-0.1%, or 0.1%-1% of one or more impurities, by weight, wherein the impurities derive from the drug substance preparation used to prepare the pharmaceutical composition. In another embodiment, the invention provides a pharmaceutical composition having from 0.001%-0.01%, 0.01%-0.1%, or 0.1%-1%, by weight, of the specific product-related impurities, process-related impurities, residual solvents and heavy metals identified herein.

In certain embodiments of this aspect, the invention provides a pharmaceutical composition having a drug substance preparation component containing (R)-(−)-2-(2-fluoro-4-biphenylyl) propionic acid, or a pharmaceutically acceptable salt thereof, as the API, admixed with one or more pharmaceutically acceptable excipients, wherein the weight of the drug substance preparation is more than about 30%, 35%, 40%, 45%, 50%, or 55% of the total weight of the pharmaceutical composition, and further having limited amounts of the impurities arising from the drug substance preparation described above. In certain embodiments of this embodiment, the drug substance preparation component can be 57% or more, 60% or more, or 63% or more of the total weight of the pharmaceutical composition. In some of these embodiments, the pharmaceutical composition is designed to contain about 200 mg or more, about 300 mg or more, about 400 mg or more, about 500 mg or more, about 600 mg or more, about 700 mg or more, about 800 mg or more of (R)-(−)-2-(2-fluoro-4-biphenylyl) propionic acid as the API in less than about 1600 mg, less than about 1500 mg, less than about 1400 mg, less than about 1300 mg, less than about 1200 mg, less than about 1100 mg, or less than about 1000 mg of pharmaceutical composition.

The invention also relates to pharmaceutical compositions and processes for making pharmaceutical compositions that exhibit one or more superior properties relative to other compositions comprising (R)-(−)-2-(2-fluoro-4-biphenylyl) propionic acid, or a pharmaceutically acceptable salt thereof, as the API. These superior properties include, but are not limited to, one or more of the following: improved bioavailability, improved solubility of the pharmaceutical composition, improved disintegration times for immediate release oral dosage forms, improved dissolution times for immediate release oral dosage forms, decreased tablet friability, increased tablet hardness, improved safety for oral dosage forms, reduced moisture content and/or hygroscopicity for oral dosage forms, improved composition wettability, improved particle size distribution of granules containing the API, improved composition compressibility, improved composition flow properties, improved chemical stability of the final oral dosage form, improved physical stability of the final oral dosage form, decreased tablet size, improved blend (or composition) uniformity, improved dose uniformity, increased granule density for wet granulated compositions, reduced water requirements for wet granulation, reduced wet granulation time, and/or reduced drying time for wet granulated mixtures.

Dosage Forms and Drug Products

In still another aspect, the invention provides dosage forms comprising therapeutically effective amounts of (R)-(−)-2-(2-fluoro-4-biphenylyl) propionic acid (or a pharmaceutically acceptable salt thereof) as the API with limited quantities of impurities arising from the drug substance used to prepare the pharmaceutical compositions used to make these dosage forms. These dosage forms can be designed for oral administration, and, in such instances, may take any acceptable form, including tablets, capsules, caplets, powders, and various granular forms. These dosage forms comprise pharmaceutical compositions that, in turn, comprise the drug substance preparations of the invention, which contain (R)-(−)-2-(2-fluoro-4-biphenylyl) propionic acid, or a pharmaceutically acceptable salt thereof, as the API, and limited amounts of impurities, as discussed above. In one embodiment, all of the impurities present in these dosage forms represent about 1%, 0.5%, 0.25% 0.1%, 0.05%, 0.025%, 0.01%, 0.005%, 0.0025%, 0.001%, or less of the total weight of the dosage form as impurities (i.e., [sum of weight(s) of impurities derived from the drug substance preparation]/[total weight of dosage form]×100%). In another embodiment, the invention provides dosage forms having from 1-0.1%, 0.1-0.01%, or 0.01-0.001% of the all the impurities arising from the drug substance preparation, as described above. In another embodiment, the invention provides a dosage form having from 1-0.001%, 0.5-0.001%, 0.25-0.001%, 0.1-0.001%, 0.05-0.001%, 0.025-0.001%, or 0.01-0.001% of one or more impurities arising from the drug substance preparation, as described above.

In certain embodiments of this aspect, the invention provides a unit dosage form having (R)-(−)-2-(2-fluoro-4-biphenylyl) propionic acid, or a pharmaceutically acceptable salt thereof, as the API, admixed with one or more pharmaceutically acceptable excipients, wherein the weight of (R)-(−)-2-(2-fluoro-4-biphenylyl) propionic acid, or the pharmaceutically acceptable salt thereof, is more than about 30%, about 35%, about 40%, about 45%, about 50%, about 55%, about 60%, about 65%, about 70% or about 75% of the total weight of the unit dosage form, and further having a limited amounts of impurities arising from the drug substance preparation used to prepare the pharmaceutical compositions used to prepare the unit dosage form. In certain embodiments, (R)-(−)-2-(2-fluoro-4-biphenylyl) propionic acid can be about 57% or more, about 58% or more, about 59% or more, about 60% or more, about 61% or more, about 62% or more, or about 63% or more of the total weight of the unit dosage form. In some of these embodiments, the unit dosage form is manufactured to administer about 200 mg, about 300 mg, about 400 mg, about 500 mg, about 600 mg, about 700 mg, or about 800 mg of (R)-(−)-2-(2-fluoro-4-biphenylyl) propionic acid, or therapeutically equivalent amount of a pharmaceutically acceptable salt thereof, as the API.

The unit dosage form of these embodiments can be provided as a unit dosage form specifically suited for oral administration (e.g., a tablet). This embodiment of the invention is manufactured using a pharmaceutical composition comprising (R)-(−)-2-(2-fluoro-4-biphenylyl) propionic acid, or a pharmaceutically acceptable salt thereof, as the API, that has from 30% to 90%, 35% to 90%, 40% to 90%, 45% to 90%, 50% to 90%, or 55% to 90% by weight API, and from 10% to 45% by weight inactive pharmaceutical ingredients, and from 2%-0.001% total (of the total weight of the dosage form) of the impurities arising from the drug substance preparation as described above. In a specific embodiment, the unit dosage form has from 55% to 85% by weight API and 15%-45% by weight inactive pharmaceutical ingredients. In another specific embodiment, the unit dosage form has from 55% to 75% by weight API and from 25% to 45% by weight inactive ingredients. In another specific embodiment, the unit dosage form has from 60% to 70% by weight API and from 30% to 40% by weight inactive pharmaceutical ingredients.

In another embodiment, the invention provides a tablet dosage form having between 320 to 480 mg (R)-(−)-2-(2- fluoro-4-biphenylyl) propionic acid, or therapeutically equivalent amount of a pharmaceutically acceptable salt thereof, as the API, where the long axis of the tablet is from about 0.50 to 0.90 inches, 0.55 to 0.8 inches, 0.6 to 0.8 inches, and the tablet width is from about 0.3 to 0.4 inches. According to this embodiment, the dosage form also has a limited amount of impurities arising from the drug substance preparation, wherein the total weight of these impurities is 1% or less of the total weight of tablet dosage form. In certain embodiments, the tablet dosage form is no longer than 0.82 inches, no longer than 0.80 inches, no longer than 0.77 inches, no longer than 0.72 inches, or no longer than 0.70 inches. In other embodiments, the tablet dosage form is no wider than 0.41 inches, no wider than 0.40 inches, no wider than 0.38 inches, or no wider than 0.35 inches. In yet another embodiment of the invention, the total volume of the tablet dosage form is less than 0.70 cm$^3$, less than 0.65 cm$^3$, less than 0.60 cm$^3$, less than 0.55 cm$^3$, less than 0.50 cm$^3$, or less than 0.45 cm$^3$.

In some embodiment, each tablet has one or more excipients chosen from disintegrants, binders, diluents, glidants, lubricants, coloring agents, stabilizers, preservatives, and/or flavoring agents. In certain embodiments, each tablet has (R)-(−)-2-(2-fluoro-4-biphenylyl) propionic acid, or a pharmaceutically acceptable salt thereof, as the API, and limited amount of impurities arising from the drug substance preparation as described above, plus one or more binders, one or more diluents, one or more disintegrants, one or more glidants, one or more lubricants, and if desired, one or more optional ingredients. In certain embodiments, the tablet dosage form is coated.

In a specific embodiment, the invention provides a tablet dosage form containing about 400 mg (R)-(−)-2-(2-fluoro-4-biphenylyl) propionic acid, or a molar equivalent amount of a pharmaceutically acceptable salt thereof, and having about 30%, 35%, 40%, 45%, 50%, or 55%, or more, by weight, of (R)-(−)-2-(2-fluoro-4-biphenylyl) propionic acid in the tablet, and limited amounts of impurities arising from the drug substance preparations as described above, wherein the total weight of the impurities in the tablet is 0.1% or less of the total weight of the tablet. The tablet dosage forms of this embodiment are specifically suited for oral administration.

In a related embodiment, the unit dosage form is a capsule dosage form. In this embodiment, the capsule dosage form has (R)-(−)-2-(2-fluoro-4-biphenylyl) propionic acid, as the API, and limited amounts of impurities arising from the drug substance preparations used to make the pharmaceutical compositions that go into the capsules, and one or more pharmaceutically acceptable excipients as additional components. With a capsule dosage form, the one or more excipients can be chosen from disintegrants, binders, diluents, glidants, lubricants, coloring agents, stabilizers, preservatives, and/or flavoring agents. In certain embodiments, the capsule dosage form comprises a hard gelatin capsule that contains a pharmaceutical composition of the invention.

In a related set of embodiments, the unit dosage form is a caplet dosage form.

The oral unit dosage forms of the present invention can contain any of the following inactive ingredients, or compounds of a similar nature: a diluent such as lactose or microcrystalline cellulose; a binder such as hydroxypropyl methylcellulose; a disintegrating agent (disintegrant) such as croscarmellose sodium or microcrystalline cellulose; a lubricant such as magnesium stearate or stearic acid; a glidant such as colloidal silicon dioxide; and optional ingredients such as coloring agents, stabilizers, preservatives, and/or flavoring agents or flavor masking agents. In addition, dosage forms of the invention can contain various other materials which modify the physical form of the dosage unit, for example, polymeric coatings (e.g., cellulosics, methacrylates, or acrylates), sugar coatings, shellac coatings, color coatings, wax coatings, or other types of coatings.

In certain embodiments, the invention provides pharmaceutical compositions having (R)-(−)-2-(2-fluoro-4-biphenylyl) propionic acid, or a pharmaceutically acceptable salt thereof, as the API, and one or more pharmaceutically acceptable excipients, with (R)-(−)-2-(2-fluoro-4-biphenylyl) propionic acid comprising about 30%, 35%, 40%, 45%, 50%, or 55% or more of the total weight of the unit dosage form. According to these embodiments, the drug substance preparation used in the compositions and dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In certain specific embodiments of the invention, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2 (fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals.

The unit dosage form of these embodiments of the invention is suited for gastrointestinal administration by an oral route (e.g., a tablet to be taken by mouth; oral administration). In some of these embodiments, (R)-(−)-2-(2-fluoro-4-biphenylyl) propionic acid is present as 57% or more, 60% or more, or 63% or more of the total weight of the of the unit dosage form. In some of these embodiments, the unit dosage form has about 100 mg, 200 mg, 300 mg, 400 mg, 600 mg, 800 mg, 1000 mg, or more, (R)-(−)-2-(2-fluoro-4-biphenylyl) propionic acid in the free acid form (or a therapeutically equivalent amount of a pharmaceutically acceptable salt thereof) contained within each unit dosage form (i.e., tablet). In one specific embodiment, approximately 400 mg of (R)-(−)-2-(2-fluoro-4-biphenylyl) propionic acid is present in a tablet dosage form as the free acid, and comprises from 65% to 68% of the total weight of the tablet dosage form.

In other embodiments of this aspect of the invention, the invention provides an (R)-(−)-2-(2-fluoro-4-biphenylyl) propionic acid-containing tablet dosage forms having from 55% to 90% by weight (R)-(−)-2-(2-fluoro-4-biphenylyl) propionic acid and from 10% to 45% by weight inactive pharmaceutical ingredients. According to this embodiment, the drug substance preparation used in preparing the tablet dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In certain specific embodiments of the invention, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2(fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals. In these embodiments, the tablet dosage form is specifically designed for oral administration.

In other embodiments of this aspect of the invention, the (R)-(−)-2-(2-fluoro-4-biphenylyl) propionic acid-containing tablet dosage form has from 55% to 85% by weight (R)-(−)-2-(2-fluoro-4-biphenylyl) propionic acid, and from 15% to 45% by weight inactive pharmaceutical ingredients. In still other embodiments of this aspect of the invention, the (R)-(−)-2-(2-fluoro-4-biphenylyl) propionic acid-containing tablet dosage form has from 55% to 75% by weight (R)-(−)-2-(2-fluoro-4-biphenylyl) propionic acid, and from 25% to 45% inactive ingredients. In still other embodiments of this aspect of the invention, the (R)-(−)-2-(2-fluoro-4-biphenylyl) propionic acid-containing tablet dosage form has from 60% to 70% by weight (R)-(−)-2-(2-fluoro-4-biphenylyl) propionic acid and from 30% to 40% inactive pharmaceutical ingredients. According to one specific embodiment of this aspect of the invention, the tablet dosage form has from 55% to 90% by weight (R)-(−)-2-(2-fluoro-4-biphenylyl) propionic acid, 1% to 20% by weight lactose (calculated based on anhydrous lactose), 1% to 20% by weight hydroxypropyl methylcellulose, 5% to 45% by weight microcrystalline cellulose, and, if desired, optional ingredients.

The (R)-(−)-2-(2-fluoro-4-biphenylyl) propionic acid-containing unit dosage forms of the present invention generally have 55% or more of the total weight of the unit dosage form as (R)-(−)-2-(2-fluoro-4-biphenylyl) propionic acid, with the remaining weight comprised of one or more pharmaceutically acceptable excipients. According to these embodiment, the drug substance used in the compositions used to manufacture the unit dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In specific embodiments, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2(fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals.

The excipients used to prepare the unit dosage forms of the invention include one or more excipients chosen from disintegrants, binders, diluents, glidants, and lubricants, as well as any desired optional ingredient. Thus, in one set of embodiments of the invention, the unit dosage form has an excipient that is a disintegrant (e.g., microcrystalline cellulose and/or croscarmellose). The amount of disintegrants in the dosage form of the invention can be 45% or less, 40% or less, 35% or less, 30% or less, or less than 25% of the total weight of the unit dosage form. In another set of embodiments of the invention, the unit dosage form has an excipient that is a binder (e.g., hydroxypropyl methylcellulose). The amount of binder in the dosage form can be 20% or less, 15% or less, 10% or less, or less than 8% of the total weight of the unit dosage form. In yet another set of embodiments of the invention, the unit dosage form has an excipient that is a diluent such as lactose. The amount of diluent in the unit dosage form can be 20% or less, 17% or less, 15% or less, or less than 12% of the total weight of the unit dosage form. In still another set of embodiments of the invention, the unit dosage form has an excipient that is a glidant such as colloidal silicon dioxide. The amount of glidant in the unit dosage form can be 7% or less, 5% or less, 3% or less, or less than 2% of the total weight of the unit dosage form. In another set of embodiments of the invention, the unit dosage form has an excipient that is a lubricant such as magnesium stearate. The amount of lubricant in the unit dosage form can be 10% or less, 5% or less, 3% or less, or less than 2% of the total weight of the unit dosage form.

In another set of embodiments of the invention, the unit dosage form, containing (R)-(−)-2-(2-fluoro-4-biphenylyl) propionic acid, or a pharmaceutically acceptable salt thereof, and one or more excipients, is coated. In one set of embodiments of the invention, the weight of the coating (e.g., Opadry Pink) is from 0.1% to 10% of the total weight of the unit dosage form. In another set of embodiments, the weight of the coating is from 0.1% to 8% of the total weight of the unit dosage form. In another set of embodiments, the weight of the coating is from 0.1% to 5% of the total weight of the unit dosage form.

In certain embodiments, the invention also provides a dosage form having between 320 to 480 mg (R)-(−)-2-(2-fluoro-4-biphenylyl) propionic acid, or a therapeutically equivalent amount of a pharmaceutically acceptable salt thereof, where the unit dosage form is no longer than 0.82 inches, no longer than 0.80 inches, no longer than 0.77 inches, no longer than 0.72 inches, or no longer than 0.70 inches, in its longest dimension. According to these embodiments, the drug substance preparation used in the dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In specific embodiments, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2(fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals. The dosage forms of this embodiment can be a unit dosage form suited for oral administration (e.g., a tablet).

In some embodiments of the invention, the unit dosage form is no wider than 0.41 inches, no wider than 0.40 inches, no wider than 0.38 inches, or no wider than 0.35 inches, in a width dimension that is perpendicular to the longest dimension. In other embodiments of the invention, the total volume of the unit dosage form is less than 0.70 cm$^3$, less than 0.65 cm$^3$, less than 0.60 cm$^3$, less than 0.55 cm$^3$, less than 0.50 cm$^3$, or less than 0.45 cm$^3$.

Unit Dosage Forms and Pharmacokinetic Profiles

The present invention also relates to (R)-(−)-2-(2-fluoro-4-biphenylyl) propionic acid-containing unit dosage forms having 55% or more by weight of (R)-(−)-2-(2-fluoro-4-biphenylyl) propionic acid that yield a pharmacokinetic profile that is substantially bioequivalent to that shown in FIG. 3 in U.S. Ser. No. 10/889,971 to Zavitz et al. filed Jul. 12, 2004 (US publication no. 20050042284). According to embodiment of this aspect of the invention, the drug substance used in the pharmaceutical compositions and dosage forms has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In specific embodiments, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2(fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals.

As used herein, substantially bioequivalent refers to Cmax (maximum plasma concentration) and AUC (area under the curve; drug exposure) parameters within 80% to 125% of the reference parameter. The unit dosage forms of these embodiments are suited for oral administration (e.g., a tablet), and in certain embodiments, the unit dosage form is a coated tablet.

In one embodiment, oral administration, to a fasting subject, of a single dose (e.g., two tablets each having 400 mg API) of the dosage forms of the present invention, provides a C max of about 25-200 μg per mL per dose; preferably 25-150 μg per mL per dose; and more preferably, between 30-95 μg per mL per dose. According to the embodiments of this aspect of the invention, the drug substance used in the compositions and dosage forms also has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In specific embodiments, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2(fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals.

In some embodiments of this aspect of the invention, oral administration of a single dose of a dosage form of the invention to a fasting subject, provides a Cmax, per dose, of greater than about 25 μg per mL, 30 μg per mL, 35 μg per mL, 40 μg per mL, 45 μg per mL, 50 μg per mL, 55 μg per mL, or 60 μg per mL. Administration of a single dose of a dosage form of the invention to a fasting subject provides an AUC (area under curve of concentration versus time; total drug exposure) of from about 200 hr·μg/mL to about 600 hr·μg/mL.

Of course, it is understood by the skilled artisan that pharmacokinetic parameters can vary substantially depending on the subject (patient taking the drug) and that these values are representative of parameters obtained from a group of subjects, rather than from one individual. See US Patent Publication No. 20050042284 (U.S. Ser. No. 10/889,971 to Zavitz et. al, filed Jul. 12, 2004) which is hereby incorporated by reference for a description of methods for obtaining these pharmacokinetic parameters.

Desirably, the dosage forms of the present invention are substantially free of (S)-(+)-2-(2-fluoro-4-biphenylyl) propionic acid. Therefore, in embodiments of dosage forms of the present invention, (R)-(−)-2-(2-fluoro-4-biphenylyl) propionic acid is present in significant excess over (S)-(+)-2-(2- fluoro-4-biphenylyl) propionic acid. In certain embodiments, (R)-(−)-2-(2-fluoro-4-biphenylyl) propionic acid is present in an enantiomeric excess of about 98.0%, 98.5%, 99.0%, 99.1%, 99.2%, 99.3%, 99.4%, 99.5%, 99.6%, 99.7%, 99.9%, or 99.9%, or more. Therefore, in these embodiments of dosage forms of the present invention, (S)-(+)-2-(2-fluoro-4-biphenylyl) propionic acid is present in less than about 1%, 0.75%, 0.5%, 0.45%, 0.4%, 0.35%, 0.3% 0.25%, 0.2%, 0.15%, 0.1%, or 0.05%, or less, by weight, of the total amount of (R)-(−)-2-(2-fluoro-4-biphenylyl) propionic acid and (S)-(+)-2-(2-fluoro-4-biphenylyl) propionic acid present in the dosage form.

In one set of preferred embodiments of the invention, a tablet unit dosage form is provided having from about 380 mg to 420 mg (R)-(−)-2-(2-fluoro-4-biphenylyl) propionic acid (or a bioequivalent amount of a pharmaceutically acceptable salt thereof), from about 50 mg to 70 mg lactose, from about 3 mg to 7 mg colloidal silicon dioxide, from about 30 mg to 50 mg hydroxypropyl methylcellulose, from about 70 mg to 105 mg microcrystalline cellulose, from about 1 mg to 5 mg croscarmellose sodium, from about 4 mg to 8 mg magnesium stearate, and optional ingredients as desired. In this preferred set of embodiments, the drug substance used to prepare the tablet unit dosage form has less than about 2%, 1%, 0.5%, 0.25% 0.1%, 0.05%, 0.025%, 0.01%, 0.005%, 0.0025%, or 0.001% of the total weight of the drug substance as one or more identified product-related impurities, process-related impurities, residual solvents, or heavy metals. In specific embodiments, the product-related impurities limited to the amounts specified above include (S)-(+)-2-(2-fluoro-4-biphenylyl) propionic acid; 2-(4-biphenylyl) propionic acid; and methyl (2-(2-fluoro-4-biphenylyl)) propionate. In other specific embodiments of the invention, the product-related impurities limited to the amounts specified above include those listed above, plus 1-phenylethyl-(2-2(fluorobiphenyl-4-yl)) propionamide. In other specific embodiments of the invention, the product-related impurities limited to the amounts specified above include those listed above, plus 1-phenylethyl-(2-2(fluorobiphenyl-4-yl)) propionamide and 2-(2-fluorobiphenyl-4-yl) propionamide. In other specific embodiments of the invention, the process-related impurities limited to the amounts specified above include (R)-(+)-α-methylbenzylamine. In other specific embodiments of the invention, the process-related impurities limited to the amounts specified above include (R)-(+)-α-methylbenzylamine and the residual solvents, including toluene, methanol and n-heptane. In yet other specific embodiments of the invention, the process-related impurities limited to the amounts specified above include (R)-(+)-α-methylbenzylamine; the residual solvents listed above, and heavy metals.

Additionally, in another set of preferred embodiments a tablet unit dosage form is provided having from about 385 mg to 415 mg (R)-(−)-2-(2-fluoro-4-biphenylyl) propionic acid, from about 55 mg to 65 mg lactose, from about 3.5 mg to 6.5 mg colloidal silicon dioxide, from about 32 mg to 48 mg hydroxypropyl methylcellulose, from about 75 mg to 100 mg microcrystalline cellulose, from about 1.5 mg to 4.5 mg croscarmellose sodium, from about 4.5 mg to 7.5 mg magnesium stearate, and optional ingredients as desired. Additionally, yet another set of preferred embodiments a tablet unit dosage form is provided having has from about 390 mg to 410 mg (R)-(−)-2-(2-fluoro-4-biphenylyl) propionic acid, from about 56 mg to 64 mg lactose, from about 4.0 mg to 6.5 mg colloidal silicon dioxide, from about 34 mg to 46 mg hydroxypropyl methylcellulose, from about 80 mg to 95 mg microcrystalline cellulose, from about 2.0 mg to 4.0 mg croscarmellose sodium, from about 5.0 mg to 7.0 mg magnesium stearate, and optional ingredients as desired. In still yet another set of preferred embodiments a tablet unit dosage form is provided having from about 395 mg to 405 mg (R)-(−)-2-(2-fluoro-4-biphenylyl) propionic acid, from about 56 mg to 64 mg lactose, from about 4.0 mg to 6.0 mg colloidal silicon dioxide, from about 34 mg to 46 mg hydroxypropyl methylcellulose, from about 82 mg to 93 mg microcrystalline cellulose, from about 2.0 mg to 4.0 mg croscarmellose sodium, from about 5.0 mg to 7.0 mg magnesium stearate, and optional ingredients as desired.

Methods for Preparing Unit Dosage Forms

There are three general methods of tablet preparation: (1) the wet-granulation method; (2) the dry-granulation method; and (3) direct compression. These methods are well known to those skilled in the art. See, *Remington's Pharmaceutical Sciences,* 16th and 18th Eds., Mack Publishing Co., Easton, Pa. (1980 and 1990). See, also, *U.S. Pharmacopeia XXI*, U.S. Pharmacopeial Convention, Inc., Rockville, Md. (1985), or the *United States Pharmacopeia—National Formulary*, USP31-NF-25, The United States Pharmacopeia (USP), Rockville, Md. (2007).

In one embodiment, the (R)-(−)-2-(2-fluoro-4-biphenylyl) propionic acid tablets can be manufactured using a high shear wet granulation method, optionally incorporating pre-blending and pre-milling. Once granulated, the material can be dried, milled and blended again. The final powder blend can be compressed into tablets on a high-speed rotary press (or any other type of tablet press) and the resulting tablets coated in a perforated pan (or in a fluid bed coating apparatus).

Soft or hard gelatin capsules can be prepared that contain a mixture of the active pharmaceutical ingredient and vegetable oil or non-aqueous, water miscible materials such as, for example, polyethylene glycol and the like. Hard gelatin capsules may contain granules of the active pharmaceutical ingredient in combination with a solid, pulverulent carrier, such as, for example, lactose, saccharose, sorbitol, mannitol, potato starch, corn starch, amylopectin, cellulose derivatives, or gelatin.

Tablets are typically made by molding, by compression, or by generally accepted tablet forming methods. Accordingly, compressed tablets are usually prepared by large-scale production methods while molded tablets often involve small-scale operations.

In one specific embodiment, tablets for oral use are typically prepared in the following manner, although other techniques may be employed.

The solid substances are ground or sieved to a desired particle size, and the binding agent is homogenized and suspended in a suitable solvent. The active pharmaceutical ingredient and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size. The operating parameters of the machine may be selected by the skilled artisan.

Various tablet formulations may be made in accordance with the present invention. These include tablet dosage forms such as sugar-coated tablets, film-coated tablets, enteric-coated tablets, multiple-compressed tablets, prolonged action tablets and the like. Sugar-coated tablets (SCT) are compressed tablets that have a sugar coating applied to the surface of the tablets subsequent to tablet formation. Such coatings may be colored and are beneficial in masking drug substances possessing objectionable tastes or odors and in protecting materials sensitive to oxidation. Film-coated tablets (FCT) are compressed tablets that have a thin layer or film of a water-soluble (or insoluble) material applied to the surface of the tablets subsequent to tablet formation. A number of polymeric substances with film-forming properties may be used. The film coating imparts the same general characteristics as a sugar coating with the added advantage of a greatly reduced time period required for the coating operation. Enteric-coated tablets are also suitable for use in the present invention. Enteric-coated tablets (ECT) are compressed tablets coated with substances that resist dissolution in gastric fluid, but that disintegrate in the intestine. Enteric coating can be used for tablets containing drug substances that are inactivated or destroyed in the stomach, for drug substances that irritate the mucosa of the stomach, or as a means of delayed release of the medication.

Multiple compressed tablets (MCT) are compressed tablets made by more than one compression cycle, such as layered tablets or press-coated tablets. Layered tablets are prepared by compressing additional tablet granulation on a previously compressed granulation. The operation may be repeated to produce multilayered tablets of two, three, or more layers. Typically, special tablet presses are required to make layered tablets. See, for example, U.S. Pat. No. 5,213,738, which is incorporated by reference herein in its entirety.

Press coated tablets are another form of multiple compressed tablets. Such tablets, also referred to as dry-coated tablets, are prepared by feeding previously compressed tablets into a tabletting machine and compressing another granulation layer around the preformed tablets. These tablets have all the advantages of compressed tablets, i.e., slotting, monogramming, speed of disintegration, etc., while retaining the attributes of sugar coated tablets in masking the taste of the drug substance in the core tablet. Press-coated tablets can also be used to separate incompatible drug substances. Further, they can be used to provide an enteric coating to the core tablets. Both types of tablets (i.e., layered tablets and press-coated tablets) may be used, for example, in the design of prolonged-action dosage forms of the present invention.

In practical use, (R)-(−)-2-(2-fluoro-4-biphenylyl) propionic acid can be combined as the active pharmaceutical ingredient in intimate admixture with a pharmaceutically acceptable carrier according to conventional pharmaceutical compounding techniques. In preparing the compositions for oral dosage form, any of the usual pharmaceutical media or excipients may be employed. These include, for example, water, glycols, oils, alcohols, flavoring agents, preservatives, coloring agents, and the like, in the case of oral liquid preparations such as suspensions, elixirs and solutions; or aerosols; or excipients such as starches, sugars, microcrystalline cellulose, diluents, granulating agents, lubricants, binders, disintegrating agents, and the like, in the case of oral solid preparations such as powders, capsules, caplets, and tablets. Solid oral preparations are generally preferred over liquid ones, for a variety of reasons, including the enhanced stability often observed for APIs in solid preparations, as compared to liquid preparations. Because of their ease of administration, tablets and capsules represent the most advantageous oral dosage unit forms, in which case solid pharmaceutically acceptable excipients are obviously employed. If desired, tablets may be coated by standard aqueous or nonaqueous techniques. Preferred solid oral preparations are tablets and capsules.

Pharmaceutical stabilizers may be used to stabilize compositions comprising (R)-(−)-2-(2-fluoro-4-biphenylyl) propionic acid, or pharmaceutically acceptable salts, solvates, or clathrates thereof. Acceptable stabilizers include, but are not limited to, L-cysteine hydrochloride, glycine hydrochloride, malic acid, sodium metabisulfite, citric acid, tartaric acid, and L-cystine dihydrochloride. See, e.g., U.S. Pat. Nos. 5,731,000; 5,763,493; 5,541,231; and 5,358,970, all of which are incorporated by reference herein in their entirety.

In general, the compositions are prepared by uniformly and intimately admixing the active pharmaceutical ingredient with a liquid pharmaceutically acceptable carrier or a finely divided solid pharmaceutically acceptable carrier, or both, and then, if necessary, shaping the product into the desired presentation. For example, a tablet may be prepared by compression or molding, optionally with one or more accessory ingredients. Compressed tablets may be prepared by compressing in a suitable machine the active pharmaceutical ingredient in a free-flowing form such as powder or granules, optionally mixed with a binder, lubricant, inert diluent, disintegrating agent, and/or surface active or dispersing agent. Molded tablets may be made by molding in a suitable machine a mixture of the powdered compound moistened with an inert liquid diluent.

The invention relates to the preparation of high drug load formulations, and processes of preparing high drug load formulations, having (R)-(−)-2-(2-fluoro-4-biphenylyl) propionic acid as the active ingredient and limited amounts of impurities. The inventors have discovered drug substance preparations of (R)-(−)-2-(2-fluoro-4-biphenylyl) propionic acid that allow for the production of (R)-(−)-2-(2-fluoro-4-biphenylyl) propionic acid unit dosage forms having 100 mg or more of API, excellent mechanical properties, therapeutically desirable dissolution and pharmacokinetic profiles, and limited amounts of impurities. The inventive formulations also allow for the production of tablets having 55% or more (R)-(−)-2-(2-fluoro-4-biphenylyl) propionic acid, by weight, yet having limited impurities. In particular, the invention relates to processes and drug substance preparations and processes useful in the preparation of such (R)-(−)-2-(2-fluoro-4-biphenylyl) propionic acid-containing unit dosage forms.

In a specific embodiment, (R)-(−)-2-(2-fluoro-4-biphenylyl) propionic acid-containing tablets can be manufactured using a high shear granulation method, optionally incorporating pre-blending and pre-milling. Once granulated, the material is dried, milled and blended again. The final powder blend (or composition) is then compressed into tablets on a high-speed rotary press and the resulting tablets are coated in a perforated pan. Bulk coated tablets are bulk-packed for shipping prior to intermediate packing for distribution to distribution centers or pharmacies, or final packaging for delivery to patients or patient caregivers.

Excipients

Inactive Pharmaceutical Ingredients

The compositions and unit dosage forms of the invention can have a number of different ingredients besides the API. Depending on the dosage strength, a unit dosage form has an amount of API sufficient for achieving a therapeutic effect in a target population. However, "inactive pharmaceutical ingredients" may also need to be present to achieve a therapeutically effective release of the API. Thus, the amount and type of inactive ingredients help achieve a therapeutically effective release of the therapeutic agent. In one aspect of the invention, a tablet unit dosage form is provided having the following inactive ingredients: one or more disintegrants in an amount sufficient to facilitate break-up (disintegration) of the tablet after administration (e.g., providing an immediate release dissolution profile), one or more binders in an amount sufficient to impart adequate cohesiveness to the tablet and/or provide adequate free flowing qualities by formulation of granules of desired size and hardness, one or more diluents in an amount sufficient to impart satisfactory compression characteristics, one or more lubricants in an amount sufficient to provide an adequate flow rate of the granulation and/or prevent adhesion of the material to the die/punch, or to reduce interparticle friction, and/or facilitate ejection from the die, and if desired, various optional ingredients to impart desired characteristics to the dosage form.

Solid pharmaceutical formulations that are compacted into a dosage form, such as a tablet, may include excipients whose functions include helping to bind the API and other excipients together after compression. Binders for solid pharmaceutical formulations include, but are not limited to, acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., Klucel®), hydroxypropyl methylcellulose (e.g., Methocel®), lactose, liquid glucose, magnesium aluminum silicate, maltodextrin, methylcellulose, polymethacrylates, povidone (e.g., Kollidon®, Plasdone®), pregelatinized starch, sodium alginate and starch. Glidants can be added to improve the flowability of a non-compacted solid formulation and to improve the accuracy of dosing. Excipients that may function as glidants include, but are not limited to, colloidal silicon dioxide, magnesium trisilicate, powdered cellulose, starch, talc and tribasic calcium phosphate.

When a dosage form such as a tablet is made by the compaction of a powdered formulation, the formulation is subjected to pressure from a punch and dye. Some excipients and active pharmaceutical ingredients have a tendency to adhere to the surfaces of the punch and dye, which can cause the product to have pitting and other surface irregularities. A lubricant can be added to the formulation to reduce adhesion and ease the release of the product from the dye. Lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Examples of diluents include, but are not limited to, calcium carbonate, calcium phosphate, calcium sulfate, cellulose, cellulose acetate, compressible sugar, confectioner's sugar, dextrates, dextrin, dextrose, ethyl cellulose, fructose, fumaric acid, glyceryl palmitostearate, hydrogenated vegetable oil, kaolin, lactitol, lactose, magnesium carbonate, magnesium oxide, maltodextrin, maltose, mannitol, microcrystalline cellulose, polydextrose, polymethylacrylates, simethicone, sodium alginate, sodium chloride, sorbitol, starch, pregelantized starch, sterilizable maize, sucrose, sugar spheres, talc, tragacanth, trehalose, and xylitol.

Examples of disintegrants include, but are not limited to, alginic acid, calcium phosphate, carboxymethyl cellulose calcium, croscarmellose, carboxymethyl cellulose sodium, powdered cellulose, chitosan, crospovidone, docusate sodium, guar gum, hydroxylpropyl cellulose, magnesium aluminum silicate, methylcellulose, povidone, sodium alginate, sodium starch glycolate, starch, and pregelantinized starch.

Example of binders (binding agents) include, but are not limited to, acacia, alginic acid, carbomers, carboxymethyl cellulose sodium, carrageenan, cellulose acetate phthalate, ceratonia, chitosan, confectioners sugar, cottonseed oil, dextrates, dextrin, dextrose, ethylcellulose, gelatin, glucose, glyceryl behenate, guar gum, hydrogenated vegetable oil, hydroxyethyl cellulose, hydroxyethylmethyl cellulose, hydroxylpropyl cellulose, hypromellose, magnesium aluminum silicate, maltodextrin, maltodextrin, maltose, methylcellulose, microcrystalline cellulose, poloxamer, polydextrose, polyethylene oxide, polymethyl acrylates, povidone, sodium alginate, starch, pregelantized starch, stearic acid, sucrose, sunflower oil, and zein.

Examples of lubricants include, but are not limited to, calcium stearate, glycerin monostearate, glyceryl behenate, glyceryl palmitostearate, hydrogenated castor oil, hydrogenated vegetable oil, light mineral oil, magnesium lauryl sulfate, magnesium stearate, medium chain triglycerides, mineral oil, poloxamer, polyethylene glycol, sodium benzoate, sodium chloride, sodium lauryl sulfate, sodium stearyl fumarate, stearic acid, talc, and zinc stearate.

Examples of glidants include, but are not limited to, calcium phosphate, calcium silicate, cellulose powdered, colloidal silicon dioxide, magnesium silicate, magnesium trisilicate, silicon dioxide, starch, and talc.

Examples of suitable pharmaceutically acceptable salts the API include, but are not limited to, aluminum, calcium, lithium, magnesium, potassium, sodium and zinc. In addition, organic salts may also be used including, but not limited to salts of lysine, N,N'-dibenzylethylenediamine, chloroprocaine, choline, diethanolamine, ethylenediamine, meglumine (N-methylglucamine), procaine and tromethamine.

Optional ingredients in the formulations of the invention include, but are not limited to, flavors, coloring agents, and stabilizers.

Flavoring agents and flavor enhancers make the dosage form more palatable to the patient. Common flavoring agents and flavor enhancers for pharmaceutical products that may be included in the formulation of the present invention include, but are not limited to, maltol, vanillin, ethyl vanillin, menthol, citric acid, fumaric acid, ethyl maltol and tartaric acid.

Solid and liquid formulations may also be dyed using any pharmaceutically acceptable colorant to improve their appearance and/or facilitate patient identification of the product and unit dosage level.

The present invention is illustrated below by reference to the following examples which set forth particularly preferred embodiments. However, it should be noted that these embodiments are illustrative and are not to be construed as limiting the invention in any way.

EXAMPLES

Example 1

Preparation of High Purity Drug Substance Comprising (R)-(−)-2-(2-fluoro-4-biphenylyl) propionic acid as the API Overview:

High purity racemic flurbiprofen (i.e., (R,S)-2-(2-fluoro-4-biphenylyl) propionic acid) used in the present invention can be produced by methods known in the art, for example, by the methods described in U.S. Pat. No. 3,755,427 or U.S. Pat.

No. 3,959,364. This high purity racemic flurbiprofen is then subjected to the resolution process generally outlined in U.S. Pat. No. 5,599,969, and more fully described below. This resolution process involves the controlled addition of the enantiopure optical resolution agent (R)-(+)-α-methylbenzylamine to racemic flurbiprofen, under conditions that facilitate the formation of the (R)-(+)-α-methylbenzylamine salts of both (R)- and (S)-(+)-2-(2-fluoro-4-biphenylyl) propionic acid. The (R)-(+)-α-methylbenzylamine salt of (R)-(−)-2-(2-fluoro-4-biphenylyl) propionic acid is then isolated by the selective crystallization process described below.

The selective crystallization process takes advantage of differences in the chemical and physical properties of the desired (R)-(+)-α-methylbenzylamine salt of (R)-(−)-2-(2-fluoro-4-biphenylyl) propionic acid, and the undesired (R)-(+)-α-methylbenzylamine salt of (S)-(+)-2-(2-fluoro-4-biphenylyl) propionic acid to efficiently resolve the two enantiomers of flurbiprofen. Once isolated as a crystalline material and washed, as described below, the (R)-(+)-α-methylbenzylamine:(R)-(−)-2-(2-fluoro-4-biphenylyl) propionic acid salt crystals are redissolved and subjected to a metathesis reaction through the addition of hydrochloric acid. The metathesis reaction liberates the (R)-(−)-2-(2-fluoro-4-biphenylyl) propionic acid as the free acid, which is then isolated by extraction and recovered by a further crystallization step.

Formation of (R)-(+)-α-methylbenzylamine salts of both (R)-(−)-2-(2-fluoro-4-biphenylyl) propionic acid and (S)-(+)-2-(2-fluoro-4-biphenylyl) propionic acid, and selective crystallization of the (R)-(+)-α-methylbenzylamine:(R)-(−)-2-(2-fluoro-4-biphenylyl) propionic acid salt Approximately 750 kg of (R,S)-2-(2-fluoro-4-biphenylyl) propionic acid (i.e., racemic flurbiprofen) was dissolved in approximately 1500 kg toluene and approximately 350 kg methanol and the mixture was warmed to 50-70° C. Approximately 500 kg of a 30-35% (w/w) solution of (R)-(+)-α-methylbenzylamine in toluene was added with mixing at a controlled rate over the course of about 30 min to form a supersaturated solution, while the temperature of the mixture was maintained around 50-70° C. After the addition of the (R)-(+)-α-methylbenzylamine, the mixture was stirred and maintained at a temperature between 50° C. and 75° C. for about 30 min, during which time (R)-(+)-α-methylbenzylamine:(R)-(−)-2-(2-fluoro-4-biphenylyl) propionic acid salt crystals formed spontaneously. The crystals were then subjected to a thermal ripening step, by raising the temperature of the mixture 5-10° C. and stirring for about 30 min. The mixture was then cooled slowly to 40-60° C., and then further cooled to between 0° C. to 5° C. The mixture was held at 0° C. to 5° C. and stirred for about 1 h. The crystals were isolated by filtration, and washed with toluene. The washed crystals were dissolved in approximately 2 to 3 times their mass of methanol and about 8 to 10 times their mass of toluene. The mixture was warmed to about 70° C. for about 15 minutes then cooled to about 60° C. After sitting for about 30 min, the solution was checked for the presence of (R)-(+)-α-methylbenzylamine:(R)-(−)-2-(2-fluoro-4-biphenylyl) propionic acid salt crystals. If crystallization had not occurred, crystallization was seeded with approximately 3 kg of (R)-(+)-α-methylbenzylamine:(R)-(−)-2-(2-fluoro-4-biphenylyl) propionic acid salt crystals. Crystals were allowed to grow for about 30 min at about 60° C. The mixture was warmed by about 5° C., and stirred for about 30 min. The mixture was cooled slowly by about 10° C., and then further cooled to between 0° C. and 5° C., and was stirred for about 1 h. The crystals were isolated by filtration, and washed with toluene.

Liberation of (R)-(−)-2-(2-fluoro-4-biphenylyl) propionic acid by metathesis with hydrochloric acid The recrystallized, washed, (R)-(+)-α-methylbenzylamine:(R)-(−)-2-(2-fluoro-4-biphenylyl) propionic acid salt crystals were dissolved in deionized water and toluene. Volumes of solvents used were of the order of 0.5-1.5 kg deionized water and 2.5-3.5 kg toluene per kg salt crystals. Approximately 0.5 kg of hydrochloric acid per kg salt crystals was added to the redissolved salt crystals, and the mixture was heated to 50-70° C., and stirred for about 30 min. The organic and aqueous layers were allowed to separate. The lower aqueous phase containing liberated (R)-(+)-α-methylbenzylamine was drawn off and the organic layer, containing the (R)-(−)-2-(2-fluoro-4-biphenylyl) propionic acid, was washed with water and hydrochloric acid to remove any remaining (R)-(+)-α-methylbenzylamine. The organic layer was subsequently washed twice with deionized water. The organic layer was heated to distil the (R)-(−)-2-(2-fluoro-4-biphenylyl) propionic acid-containing toluene mixture and reduce the volume to approximately 2-3 kg of solvent per kg of salt crystals originally dissolved before acidification.

Crystallization of (R)-(−)-2-(2-fluoro-4-biphenylyl) propionic acid and isolation of the drug substance After distillation, the remaining solution was cooled to 30-35° C., creating a supersaturated solution of (R)-(−)-2-(2-fluoro-4-biphenylyl) propionic acid, which was stirred for about 30 min. If crystallization of (R)-(−)-2-(2-fluoro-4-biphenylyl) propionic acid did not occur spontaneously, crystallization was seeded with 1-3 kg of (R)-(−)-2-(2-fluoro-4-biphenylyl) propionic acid crystals. Crystallization was allowed to continue for about 30 min at 25-35° C. Following this initial crystallization period, the mixture was then slowly cooled to below 0° C. and held for about 1 h with stirring. The crystalline (R)-(−)-2-(2-fluoro-4-biphenylyl) propionic acid was collected by filtration and washed with cold n-heptane. The drug substance preparation was obtained by drying the solid under vacuum at about 60° C.

Example 2

Determination of API Content and Selected Product-Related Impurities by HPLC

Reagents and Solutions

Reagents: Acetonitrile (HPLC grade) and glacial acetic acid (analytical reagent grade).

Mobile phase: Add 50 ml of glacial acetic acid to 350 ml (±10 ml) of acetonitrile, dilute to 1 liter with water and mix. Filter and degas using a suitable technique.

Sample solvent: Add 450 ml acetonitrile to a 1 liter flask and dilute to volume with water and mix. Filter and degas using a suitable technique.

Test mixture: Dissolve 10 mg of cis-2-(2-fluoro-4-biphenylyl)-2,3-dimethylsuccinic acid, 2-(4-biphenylyl) propionic acid, methyl 2-(2-fluorobiphenyl-4-yl) propionate and N-1-phenylethyl-2-(2-fluorobiphenyl-4-yl) propionamide in 100 ml acetonitrile and mix. To 1.0 ml of this solution add about 100 mg of (R)-(−)-2-(2-fluoro-4-biphenylyl) propionic acid assay reference standard, and dilute to 100 ml using sample solvent.

Preparation of Standard Solutions:

Standard solution 1: Weigh accurately 100 mg of (R)-(−)-2-(2-fluoro-4-biphenylyl) propionic acid assay reference standard (±5 mg) and transfer to a 100 ml volumetric flask. Dilute to volume with sample solvent.

Standard solution 2: Weigh accurately 100 mg of (R)-(−)-2-(2-fluoro-4-biphenylyl) propionic acid assay reference standard (±5 mg) and transfer to a 100 ml volumetric flask. Dilute to volume with sample solvent.

Preparation of Sample Solution:

Dissolve 100 mg (±5 mg) of drug substance preparation in 100 ml of sample solvent.

Chromatographic Conditions:

| | |
|---|---|
| Column: | Waters 5 μm C18 Resolve column, 150 mm long and 3.9 mm internal diameter. |
| Flow rate: | 1.0 ml per minute. (*) |
| Detector: | Ultraviolet, wavelength set at 254 nm. |
| Temperature: | 35° C. |
| Run Time: | 45 mins |
| Volume injected: | 5 μl. |

Note:

It may be necessary to condition the column with a series of sample injections prior to use.

(*): Adjust the flow rate to give a retention time of the (R)-(−)-2-(2-fluoro-4-biphenylyl) propionic acid peak of about 10 minutes and optimize separation between impurities.

Injection Sequence:

TABLE 1

Injection Sequence

| Sequence | Number of injections |
|---|---|
| Test mix | 2 |
| Blank | 1 |
| Standard solution 1 | 6 |
| Standard solution 2 | 2 |
| Sample 1 | 2 |
| Sample 2 | 2 |
| Standard solution 1* | 2 |
| Sample 3 | 2 |
| Sample 4 | 2 |

*An injection of the standard solution must be made at least every four injections.

System Suitability:

1. The system is suitable if the resolution between the 2-(4-Biphenylyl) propionic acid peak and the (R)-(−)-2-(2-fluoro-4-biphenylyl) propionic acid peak is at least 1.5;

2. The percentage relative standard deviation on the six standard injections at the start of the run must be not greater than 2%; and 3. The percentage difference between the mean peak area of standard solution 1 and standard solution 2 must be between 98.0 and 102.0%.

Calculation of the Content of (R)-(−)-2-(2-fluoro-4-biphenylyl) propionic acid

Determine the mean peak area of standard and sample solutions and calculate the percentage (R)-(−)-2-(2-fluoro-4-biphenylyl) propionic acid content in the sample as follows:

$$\% \text{ w/w } (R)\text{-}2\text{-}(2\text{-fluoro-4-biphenylyl)propionic acid} = \frac{\text{mean peak area of sample} \times \text{weight of standard (g)} \times \text{standard purity}}{\text{mean peak area standard solution 1} \times \text{weight of sample (g)}}$$

Determination of Product-Related Impurity Content of Drug Substance Preparation:

Measure the areas of the (R)-(−)-2-(2-fluoro-4-biphenylyl) propionic acid peak and of each related substance (product-related impurity) peak and calculate the percentage of each as follows:

$$\% \text{ impurity} = \frac{\text{area of related substance peak} \times f \times 100}{\text{corrected total area of all peaks}}$$

Where f is the correction factor specific to each product-related impurity.

The correction factors of selected product-related impurities and their retention times relative to (R)-(−)-2-(2-fluoro-4-biphenylyl) propionic acid are given below.

TABLE 2

Correction Factors

| Chemical name | Relative retention time | Correction factor (f) |
|---|---|---|
| cis-2-(2-Fluoro-4-biphenylyl)-2,3-dimethylsuccinic acid | 0.80 | 1.323 |
| 2-(4-Biphenylyl) propionic acid | 0.90 | 0.727 |
| (R)-(−)-2-(2-fluoro-4-biphenylyl) propionic acid (API) | 1.0 | 1.0 |
| Methyl (2-(2-fluoro-4-biphenylyl))propionate | 2.99 | 1.132 |
| 1-Phenylethyl-(2-(2-fluorobiphenyl-4-yl))propionamide | 3.11 | 1.430 |

Determination of Optical (Enantiomeric) Purity:

Reagents: Propan-2-ol, n-heptane, trifluoroacetic acid (use HPLC grade materials).

Mobile Phase: To 70 ml of Propan-2-ol add 1.0 ml of trifluoroacetic acid, dilute to 1 liter in n-heptane. Mix and degas using a suitable method.

Sample Solvent: Add 100 ml of propan-2-ol to 900 ml of n-heptane. Mix and degas using a suitable method.

Preparation of the sample solution: Weigh 12 mg (±1 mg) of drug substance preparation and transfer to a 100 ml volumetric flask. Dissolve in 1.0 ml of methanol and fill to volume with sample solvent.

System Suitability:

Resolution:

Test Solution 1: Weigh 30 mg (±1 mg) of the racemic flurbiprofen and transfer to a 100 ml volumetric flask. Dissolve in 1.0 ml of methanol and fill to volume with sample solvent. Dilute 1.0 ml of the solution with sample solvent to make 100 ml (this is equivalent to 0.15 mg of each enantiomer per 100 ml of solution and corresponds to 1.25% with reference to the test solution). The resolution between the R-enantiomer and the S-enantiomer should be not less than 2.5.

Sensitivity Testing:

Test Solution 2: Dilute 2.0 ml of system suitability test solution 1 with sample solvent to make 10.0 ml (this is equivalent to 0.03 mg of each enantiomer per 100 ml of solution and corresponds to 0.25% with reference to the test solution). Adjust the chromatographic axes such that it is possible to measure the signal for the R-enantiomer and the signal of unaffected baseline. The signal for the R-enantiomer should be not less than 3 times that of unaffected baseline.

Chromatographic Conditions:

| | |
|---|---|
| Column: | Chiralpak AD, 250 mm × 4.6 mm internal diameter, or equivalent. |
| Flow rate: | 0.8 ml per minute. |
| Detector: | Ultraviolet, wavelength set at 247 nm. |
| Temperature: | 25° C. |
| Run Time: | 30 mins. |
| Volume injected: | 10 µl. |

Using the above specified conditions, inject test solution 1, test solution 2, sample solvent and sample solution. Determine the enantiomeric excess by two replicate injections of sample solution.

The retention times of the enantiomers are as follows:

TABLE 3

Enantiomer Retention Times

| Enantiomer | Relative Retention Time |
|---|---|
| (R)-(−)-2-(2-fluoro-4-biphenylyl) propionic acid | 1.00 |
| (S)-(+)-2-(2-fluoro-4-biphenylyl) propionic acid | 1.30 |

Calculation of Enantiomeric Excess:

Measure the areas of the peaks due to the R(−) and S(+) enantiomers and calculate the enantiomeric excess as follows:

$$\% \, EE(R) = \left[ \frac{\text{Area } R(-)}{\text{Area } R(-) + \text{Area } S(+)} - \frac{\text{Area } S(+)}{\text{Area } R(-) + \text{Area } S(+)} \right] \times 100\%$$

Example 3

Selected Impurities in Exemplary Batch of Drug Substance

Two batches of drug substance (i.e., a drug substance preparation) were prepared using the chiral crystallization protocol as outlined in Example 1, and assayed using the techniques described in Example 2. Batch A resulted in 187 kg of drug substance, with an optical purity (enantiomeric excess of (R)-(−)-2-(2-fluoro-4-biphenylyl) propionic acid over (S)-(+)-2-(2-fluoro-4-biphenylyl) propionic acid) of 99.7% ee. Batch B resulted in 300 kg of drug substance, with an optical purity (enantiomeric excess of (R)-(−)-2-(2-fluoro-4-biphenylyl) propionic acid over (S)-(+)-2-(2-fluoro-4-biphenylyl) propionic acid) of 99.9% ee. Table 4 provides the results of the assays for impurities conducted on these two batches of drug substance.

TABLE 4

Selected Impurities in Two Exemplary Batches of Drug Substance.

| Impurity | Amount Batch A | Amount Batch B |
|---|---|---|
| Product-Related: | | |
| (S)-(+)-2-(2-fluoro-4-biphenylyl) propionic acid | 0.15% * | 0.05% * |
| 2-(4-biphenylyl) propionic acid | 0.11% | 0.07% |
| methyl (2-(2-fluoro-4-biphenylyl)) propionate | none detected | 0.02% |
| Total Product-Related Impurities (excluding (S)-(+)-flurbiprofen) | 0.1% | 0.1% |
| Process-Related: | | |
| (R)-(+)-α-methylbenzylamine | <50 ppm | <50 ppm |
| Residual Solvents: | | |
| toluene | <100 ppm | none detected |
| methanol | <0.01% | 0.01% |
| n-heptane | <0.01% | <0.01% |
| Heavy Metals | <10 ppm | <10 ppm |
| Content of both enantiomers of 2-(2-fluoro-4-biphenylyl) propionic acid by HPLC | 99.9% | 98.1% |
| Content of both enantiomers of 2-(2-fluoro-4-biphenylyl) propionic acid by titration | 100.0% | 99.9% |

* Value calculated from optical purity (enantiomeric excess of (R)-(−)-2-(2-fluoro-4-biphenylyl) propionic acid over (S)-(+)-2-(2-fluoro-4-biphenylyl) propionic acid, where optical purity of Batch A = 99.7% ee, and optical purity of Batch B = 99.9% ee.

Example 4

Components of an (R)-(−)-2-(2-fluoro-4-biphenylyl) propionic acid-Containing Tablet Dosage Form The components of this tablet dosage form are given in Table 5 below. The quantitative composition in both the batch preparation and in the individual tablets are given in Table 6, while an exemplary method of making the tablets is described in Example 5, and methods used for analyzing the API and selected product-related impurities in the drug substance used to prepare the tablets, were given in Example 2. Table 7 provides relevant physical properties of the secondary granulation composition that is compressed into the tablets that are subsequently coated. Table 8 provides relevant physical properties of the compressed tablets. Table 9 provides the dissolution profile of a representative sample of coated tablets.

TABLE 5

Components of 400 mg Tablets

| Component | Specification/grade |
|---|---|
| Drug substance preparation | Manufacturer's specification |
| Lactose, anhydrous | EP, USP |
| Colloidal silicon dioxide (Cab-O-Sil M5P) | EP, USP |
| Hydroxypropyl methylcellulose E-5 | EP, USP |
| Microcrystalline cellulose (Avicel PH 302) | EP, USP |
| Croscarmellose sodium Type A (Ac-Di-Sol) | EP, USP |
| Magnesium stearate, non-bovine | EP, USP |
| Water, purified | EP, USP |
| Opadry Pink 03K94003 | In-house specification |

TABLE 6

Quantitative Composition of (R)-(−)-2-(2-fluoro-4-biphenylyl) propionic acid 400 mg Tablets

| Component | Weight (mg/tablet) | Representative batch (grams/batch) |
|---|---|---|
| Drug Substance Preparation | 400.00 | 300,000 |
| Lactose, anhydrous | 59.60 | 44,700 |
| Colloidal silicon dioxide (Cab-O-Sil M5P) | 2.70 | 2,025 |
| Hydroxypropyl methylcellulose E-5 | 39.00 | 29,250 |
| Water, purified | Essentially removed during drying | 70,200[1] |
| Total Primary Granulation Composition: | | 375,975 |
| Primary Granulation Composition | | 375,975 |
| Microcrystalline cellulose (Avicel PH 302) | 87.00 | 65,250 |
| Croscarmellose sodium (Ac-Di-Sol) | 3.00 | 2,250 |
| Colloidal silicon dioxide (Cab-O-Sil M5P) | 2.70 | 2,025 |
| Magnesium stearate, non-bovine | 6.00 | 4,500 |
| Total Secondary Granulation Composition (for compression): | | 450,000 |
| Secondary Granulation Composition (tablet core) | | 450,000 |
| Opadry Pink 03K94003 coating | 18.56 | 13,920 |
| Water, purified | Essentially removed during drying | 102,075 |
| Final Dosage Form (Tablet(s)): | 618.6 | 463,920 |

TABLE 7

Secondary Granulation Composition Properties

| Bulk Density: | 0.51 g/ml |
|---|---|
| Tap Density: | 0.62 g/ml |
| Flow Rate Index: | 4.664 kg/sec |

Sieve Analysis

| Mesh Size | Percent Retained |
|---|---|
| 40 mesh: | 22% |
| 80 mesh: | 45% |
| 100 mesh: | 6% |
| 140 mesh: | 8% |
| 200 mesh: | 6% |
| 325 mesh: | 7% |
| Pan: | 6% |

TABLE 8

Core Tablet Physical Properties

| Weight Variation | 0.598 g avg. (1.11% RSD) |
|---|---|
| Hardness | 15.2 kp avg. (3.8% RSD) |
| Thickness | 5.30 mm avg. (0.54% RSD) |

Friability: 100 rev. = 0.28%; 400 rev. = 0.82%

TABLE 9

Coated Tablet Disintegration and Dissolution

| Actual Film Coat | 2.20% by wt |
|---|---|
| Disintegration (min:sec) | 22:55, 24:15, 26:30 |

Dissolution

| Time | Percent (RSD) |
|---|---|
| 15 min: | 51.9% (8.0) |
| 30 min.: | 96.1% (1.2) |
| 45 min.: | 98.5% (1.5) |
| 60 min.: | 99.0% (1.4) |
| 90 min.: | 99.4% (1.2) |

The unit dosage form of Example 4 is an example of one preferred unit dosage form of the invention. Thus the unit dosage form can, for example, exhibit greater than 50% release of API at 15 min, greater than 66% release of API at 30 min, greater than or equal to 75% release of API at 45 min, greater than or equal to 90% release of API at 60 min, and greater than or equal to 99% release of API at 90 min.

Example 5

Process for Preparing (R)-(−)-2-(2-fluoro-4-biphenylyl) propionic acid Containing Tablet Dosage Forms The tablet unit dosage form of Example 4 was manufactured according to the following process.

The manufacturing procedure was a high shear granulation process. Once granulated, the material was dried, milled and blended again. The final powder blend (i.e., secondary granulation composition) was compressed into tablets on a high-speed rotary press and the resulting tablets were coated in a perforated pan.

An outline of the manufacturing is provided below:
1. Charge the lactose anhydrous, (R)-(−)-2-(2-fluoro-4-biphenylyl) propionic acid drug substance, and colloidal silicon dioxide into a drum-type blender.
2. Blend components together for a sufficient amount of time (e.g., 5 min) and discharge into a mill (e.g., Comil U20 or equivalent).
3. Mill through a sufficient size screen (e.g., 0.018"). Discharge into a high shear granulator (e.g., Fielder PMA300 (Eastleigh, Hampshire, United Kingdom) or equivalent).
4. Charge the hydroxypropyl methylcellulose into the high shear granulator and dry blend (approximately 3 min).
5. Granulate material using purified water (e.g., 14.5% to 18.9% (or 23%) of the dry weight materials; granulated on Setting 1 for approximately 10 min).
6. Mill the wet granulation through an appropriate size screen (e.g., Comil U20 or equivalent; 0.250" screen).
7. Dry the milled granulation (e.g., Aeromatic T5 fluid bed (Eastleigh, Hampshire, United Kingdom) or equivalent; ca. 70° C. inlet, ca. 30° C. outlet; dry to LOD <2.0%; ca. 20-25 min).
8. Mill the dried granulation through an appropriate size screen (e.g., Comil U20 (available from Quadro, Waterloo, Ontario, Canada) or equivalent; 0.055" screen).

Note: Steps 1-8 may be performed as sub-lot granulations to enable adjustment of batch size. Also, blending of steps 1-4 may occur in the high shear granulator without any prior blending or milling.

9. Charge dried granulation along with microcrystalline cellulose, croscarmellose sodium, and colloidal silicon dioxide into a diffusion blender (e.g., Bohle PM1000 or equivalent). Blend the material for an appropriate amount of time (e.g., 25 min at 6 rpm).
10. Charge the magnesium stearate into the diffusion blender. Blend for an appropriate amount of time (e.g., 5 min at 6 rpm).
11. Compress the blended powders on a high-speed rotary press into 600 mg (total tablet weight) modified oval tablets debossed with MY4.
12. Prepare the film-coating suspension by mixing Opadry Pink into purified water for a 12% by weight solids concentration.
13. Film coat tablets with Opadry Pink in a perforated coating pan (e.g., Lodige LHC130 Hi-Coater) to a theoretical weight gain of approximately 3%.

Note: Steps 12-13 may be performed as sub-lot coatings, in which case step 14 (consolidation of sub-lots) is required.
14. Consolidate sub-lots as necessary.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A drug substance preparation comprising (R)-(−)-2-(2-fluoro-4-biphenylyl) propionic acid, or a pharmaceutically acceptable salt thereof, as the active pharmaceutical ingredient, and between about 0.001% and about 3%, by weight, product-related impurities, wherein said product-related impurities comprise not more than about 0.5%, by weight, 2-(4-biphenylyl) propionic acid, or a salt thereof, and not more than about 2%, by weight, of the enantiomeric impurity (S)-(+)-2-(2-fluoro-4-biphenylyl) propionic acid, or a salt thereof, and not more than about 200 ppm of the process-related impurity, (R)-(+)-α-methylbenzylamine.

2. The drug substance preparation of claim 1 wherein said product-related impurities further comprise not more than about 0.1%, by weight, methyl (2-(2-fluoro-4-biphenylyl)) propionate, or a salt thereof.

3. The drug substance preparation of claim 1, wherein said product-related impurities comprise not more than about 1%, by weight, of the enantiomeric impurity (S)-(+)-2-(2-fluoro-4-biphenylyl) propionic acid, or a salt thereof.

4. The drug substance preparation of claim 1, wherein said product-related impurities comprise not more than about 0.5%, by weight, of the enantiomeric impurity (S)-(+)-2-(2-fluoro-4-biphenylyl) propionic acid, or a salt thereof.

5. A pharmaceutical composition comprising the drug substance preparation of claim 4, and one or more excipients.

6. A drug product or dosage form comprising the pharmaceutical composition of claim 5 and one or more additional excipients.

7. The drug product or dosage form of claim 6, wherein the drug product or dosage form is a tablet formulated to orally administer at least about 100 mg of (R)-(−)-2-(2-fluoro-4-biphenylyl) propionic acid, or the molar equivalent amount of a salt thereof.

8. The drug product or dosage form of claim 6, wherein the drug product or dosage form is a tablet formulated to orally administer at least about 200 mg of (R)-(−)-2-(2-fluoro-4-biphenylyl) propionic acid, or the molar equivalent amount of a salt thereof.

9. The drug product or dosage form of claim 6, wherein the drug product or dosage form is a tablet formulated to orally administer at least about 400 mg of (R)-(−)-2-(2-fluoro-4-biphenylyl) propionic acid, or the molar equivalent amount of a salt thereof.

10. The drug product or dosage form of claim 6, wherein the drug product or dosage form is a tablet formulated to orally administer at least about 800 mg of (R)-(−)-2-(2-fluoro-4-biphenylyl) propionic acid, or the molar equivalent amount of a salt thereof.

11. The drug substance preparation of claim 1 further comprising not more than about 50 ppm of the process-related impurity, (R)-(+)-α-methylbenzylamine.

12. The drug substance preparation of claim 11 further comprising residual solvents of not more than about 890 ppm of toluene, not more than about 0.3%, by weight, methanol, and not more than about 0.3%, by weight, n-heptane.

13. The drug substance preparation of claim 12 further comprising not more than about 10 ppm lead.

14. A unit dosage form comprising 55-90%, by weight, drug substance preparation of claim 4 and 10-45% total, by weight, of one or more excipients, wherein said unit dosage form contains 100 mg or more of (R)-(−)-2-(2-fluoro-4-biphenylyl) propionic acid, or the molar equivalent amount of a salt thereof.

15. The unit dosage form of claim 14 having from about 200 to about 800 mg (R)-(−)-2-(2-fluoro-4-biphenylyl) propionic acid, or the molar equivalent amount of a salt thereof.

16. The unit dosage form of claim 14 having from about 300 to about 500 mg (R)-(−)-2-(2-fluoro-4-biphenylyl) propionic acid, or the molar equivalent amount of a salt thereof.

17. The unit dosage form of claim 16 having about 400 mg (R)-(−)-2-(2-fluoro-4-biphenylyl) propionic acid, or the molar equivalent amount of a salt thereof.

18. The unit dosage form of claim 17, wherein said unit dosage form is a tablet.

19. The unit dosage form of claim 16, wherein the total weight of said dosage form is no more than about 800 mg.

20. The unit dosage form of claim 16, wherein the total weight of said dosage form is no more than about 700 mg.

21. The unit dosage form of claim 14, wherein said one or more excipients comprises microcrystalline cellulose.

22. The unit dosage form of claim 14, wherein said (R)-(−)-2-(2-fluoro-4-biphenylyl) propionic acid is the free acid form of (R)-(−)-2-(2-fluoro-4-biphenylyl) propionic acid.

23. The unit dosage form of claim 14, wherein said dosage form is a tablet or a capsule.

24. The unit dosage form of claim 14, wherein said dosage form is a tablet.

25. A drug substance preparation comprising:
  (1) (R)-(−)-2-(2-fluoro-4-biphenylyl) propionic acid, or a pharmaceutically acceptable salt thereof, as the active pharmaceutical ingredient;
  (2) between about 0.001% and about 2%, by weight, product-related impurities, wherein said product-related impurities comprise:
    (a) not more than about 0.5%, by weight, 2-(4-biphenylyl) propionic acid,
    (b) not more than about 0.1%, by weight, methyl (2-(2-fluoro-4-biphenylyl)) propionate, and (c) not more than about 1.0%, by weight, of the enantiomeric impurity (S)-(+)-2-(2-fluoro-4-biphenylyl) propionic acid, or a salt thereof;

(3) not more than about 200 ppm of the process-related impurity, (R)-(+)-α-methylbenzylamine;

(4) not more than about 900 ppm of toluene, not more than about 0.3%, by weight, methanol, and not more than about 0.3%, by weight, n-heptane; and (5) not more than about 10 ppm lead.

26. The drug substance preparation of claim 25, wherein said product-related impurities comprise not more than about 0.5%, by weight, of the enantiomeric impurity (S)-(+)-2-(2-fluoro-4-biphenylyl) propionic acid, or a salt thereof.

27. A pharmaceutical composition comprising the drug substance preparation of claim 26, and one or more excipients.

28. A drug product or dosage form comprising the pharmaceutical composition of claim 27 and one or more additional excipients.

29. The drug product or dosage form of claim 28, wherein the drug product or dosage form is a tablet formulated to orally administer at least about 100 mg of (R)-(−)-2-(2-fluoro-4-biphenylyl) propionic acid, or the molar equivalent amount of a salt thereof.

30. The drug product or dosage form of claim 28, wherein the drug product or dosage form is a tablet formulated to orally administer at least about 200 mg of (R)-(−)-2-(2-fluoro-4-biphenylyl) propionic acid, or the molar equivalent amount of a salt thereof.

31. The drug product or dosage form of claim 28, wherein the drug product or dosage form is a tablet formulated to orally administer at least about 400 mg of (R)-(−)-2-(2-fluoro-4-biphenylyl) propionic acid, or the molar equivalent amount of a salt thereof.

32. The drug product or dosage form of claim 28, wherein the drug product or dosage form is a tablet formulated to orally administer at least about 800 mg of (R)-(−)-2-(2-fluoro-4-biphenylyl) propionic acid, or the molar equivalent amount of a salt thereof.

33. The drug substance preparation of claim 25, wherein the drug substance preparation comprises not more than about 50 ppm of the process-related impurity, (R)-(+)-α-methylbenzylamine.

* * * * *